(12) United States Patent
Wakamatsu et al.

(10) Patent No.: US 11,225,683 B2
(45) Date of Patent: Jan. 18, 2022

(54) PHOTOCOUPLING METHOD USING PROBE CONTAINING PHOTORESPONSIVE NUCLEIC ACIDS

(71) Applicant: LSI Medience Corporation, Tokyo (JP)

(72) Inventors: Hirotake Wakamatsu, Tokyo (JP); Akira Yanagihara, Tokyo (JP); Hiroshi Terasaki, Tokyo (JP); Nobutake Fugono, Tokyo (JP); Mitsunobu Shimadzu, Tokyo (JP); Kenzo Fujimoto, Ishikawa (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 573 days.

(21) Appl. No.: 14/414,643

(22) PCT Filed: Jul. 19, 2013

(86) PCT No.: PCT/JP2013/069694
§ 371 (c)(1),
(2) Date: Apr. 8, 2015

(87) PCT Pub. No.: WO2014/014106
PCT Pub. Date: Jan. 23, 2014

(65) Prior Publication Data
US 2015/0211057 A1 Jul. 30, 2015

(30) Foreign Application Priority Data

Jul. 20, 2012 (JP) .............................. JP2012-161834
Dec. 11, 2012 (JP) .............................. JP2012-270614

(51) Int. Cl.
*C12Q 1/6827* (2018.01)
*C12Q 1/6816* (2018.01)

(52) U.S. Cl.
CPC ......... *C12Q 1/6827* (2013.01); *C12Q 1/6816* (2013.01)

(58) Field of Classification Search
None
See application file for complete search history.

(56) References Cited

U.S. PATENT DOCUMENTS

2007/0269825 A1* 11/2007 Wang .................. C12Q 1/6858
435/5
2010/0274000 A1 10/2010 Fujimoto et al.
2011/0033855 A1 2/2011 Hori et al.
2011/0034683 A1 2/2011 Fujimoto et al.
2013/0177918 A1* 7/2013 Terasaki ............... C12Q 1/6858
435/6.12

FOREIGN PATENT DOCUMENTS

| JP | 2009-254279 | 11/2009 | |
|---|---|---|---|
| JP | 2011-036150 A | 2/2011 | |
| JP | 2012-121899 | 6/2012 | |
| WO | WO-2005072133 A2 * | 8/2005 | ........... C12Q 1/6816 |
| WO | 2012-033190 A1 | 3/2012 | |

OTHER PUBLICATIONS

Sasaki et al. (CHem Soc Rev 2011 vol. 40 p. 5698-5706).*
Yoshinaga Yoshimura et al., "Hikari Oto Gata Kakusan Probe o Mochiita Ine Genome SNPs Kaiseki", CSJ: The Chemical Society of Japan Koen Yokoshu, vol. 91(4), p. 1579 (1 PC-091) (2011).
Yoshinaga Yoshimura et al., "Ultrafast Reversible Photo-Cross-Linking Reaction: Toward in Situ DNA Manipulation", Organic Letters, vol. 10 (15), pp. 3227-3230 (2008).
Yoshinaga Yoshimura et al., The Chemical Society of Japan Koen Yokoshu, vol. 91, No. 4, p. 1579, Mar. 11, 2011.
International Search Report for PCT/JP2013/069694 dated Oct. 22, 2013.

* cited by examiner

*Primary Examiner* — Katherine D Salmon
(74) *Attorney, Agent, or Firm* — Heslin Rothenberg Farley & Mesiti P.C.

(57) ABSTRACT

Provided are: a photocoupling method that overcomes the problem of the stagnation of photocoupling with a target nucleotide using a probe containing a photo-responsive nucleotide, and that improves the photocoupling efficiency; and a photocoupling kit.

The photocoupling method is characterized by hybridizing a target site present in a nucleic acid sample with a first probe having a sequence complementary to the target site and containing a photo-responsive nucleotide, in a reaction solution, and carrying out photocoupling by photo-irradiation, wherein self-assembly caused by the photo-responsive nucleotide contained in the first probe is suppressed. The photocoupling kit is characterized by comprising a first probe having a sequence complementary to a target site present in a nucleic acid sample, and containing a photo-responsive nucleotide; and a second probe being highly complementary to the first probe.

14 Claims, 10 Drawing Sheets
Specification includes a Sequence Listing.

PREPd.
5'- CGCACCCAGCAXTTTG -3'

PREP-A
5'- AAXAAAAAAAAAAAAA -3'

PREP-G

5'- GGXGGGGGGGGGGGGGG -3'

PREP-AG

5'- AGXAGAGAGAGAGAGA -3'

(1) L861

| PREP | Sequence |
|---|---|
| L861 AS strand | 3' -<u>GAC</u>XACCCACGCCTTCTC-5' |
| L861 S strand | 5' -TTGGGCTGGCCAAX<u>CTG</u>C-3' |

(2) T790

| PREP | Sequence |
|---|---|
| T790 AS strand | 3' -GAGTAG<u>TGC</u>GTCXAGT-5' |
| T790 S strand | 5' -CAXCTCATC<u>ACG</u>CAGC-3' |

(3) L858

| PREP | Sequence |
|---|---|
| L858 AS strand | 3' -CCC<u>GAC</u>CGGTTTXAC-5' |
| L858 S strand | 5' -GAXTTTGGG<u>CTG</u>GCCA-3' |

Underlined: Target site (1) L861

(2) T790

(3) L858

```
                              SEQUENCE LISTING

<160> NUMBER OF SEQ ID NOS: 32

<210> SEQ ID NO 1
<211> LENGTH: 100
<212> TYPE: DNA
<213> ORGANISM: Homo sapiens

<400> SEQUENCE: 1
agccaggaac gtactggtga aaacaccgca gcatgtcaag atcacagatt ttgggctggc      60
caaactgctg ggtgcggaag agaaagaata ccatgcagaa                          100

<210> SEQ ID NO 2
<211> LENGTH: 16
<212> TYPE: DNA
<213> ORGANISM: Artificial Sequence
<220> FEATURE:
<223> OTHER INFORMATION: probe PREPa.
<220> FEATURE:
<221> NAME/KEY: misc_feature
<222> LOCATION: (6)..(6)
<223> OTHER INFORMATION: "n" is CNVK

<400> SEQUENCE: 2
cagcantttg gccagc                                                     16

<210> SEQ ID NO 3
<211> LENGTH: 16
<212> TYPE: DNA
<213> ORGANISM: Artificial Sequence
<220> FEATURE:
<223> OTHER INFORMATION: probe PREPb.
<220> FEATURE:
<221> NAME/KEY: misc_feature
<222> LOCATION: (8)..(8)
<223> OTHER INFORMATION: "n" is CNVK

<400> SEQUENCE: 3
cccagcantt tggcca                                                     16

<210> SEQ ID NO 4
<211> LENGTH: 16
<212> TYPE: DNA
<213> ORGANISM: Artificial Sequence
<220> FEATURE:
<223> OTHER INFORMATION: probe PREPc.
<220> FEATURE:
<221> NAME/KEY: misc_feature
<222> LOCATION: (10)..(10)
<223> OTHER INFORMATION: "n" is CNVK

<400> SEQUENCE: 4
cacccagcan tttggc                                                     16

<210> SEQ ID NO 5
<211> LENGTH: 16
<212> TYPE: DNA
<213> ORGANISM: Artificial Sequence
<220> FEATURE:
<223> OTHER INFORMATION: probe PREPd.
<220> FEATURE:
<221> NAME/KEY: misc_feature
```

```
<222> LOCATION: (12)..(12)
<223> OTHER INFORMATION: "n" is CNVK

<400> SEQUENCE: 5
cgcacccagc antttg                                                    16

<210> SEQ ID NO 6
<211> LENGTH: 21
<212> TYPE: DNA
<213> ORGANISM: Homo sapiens

<400> SEQUENCE: 6
gaacgtactg gtgaaaacac c                                              21

<210> SEQ ID NO 7
<211> LENGTH: 21
<212> TYPE: DNA
<213> ORGANISM: Homo sapiens

<400> SEQUENCE: 7
gcatggtatt ctttctcttc c                                              21

<210> SEQ ID NO 8
<211> LENGTH: 16
<212> TYPE: DNA
<213> ORGANISM: Artificial Sequence
<220> FEATURE:
<223> OTHER INFORMATION: probe PREP-A
<220> FEATURE:
<221> NAME/KEY: misc_feature
<222> LOCATION: (3)..(3)
<223> OTHER INFORMATION: "n" is CNVK

<400> SEQUENCE: 8
aanaaaaaaa aaaaaa                                                    16

<210> SEQ ID NO 9
<211> LENGTH: 16
<212> TYPE: DNA
<213> ORGANISM: Artificial Sequence
<220> FEATURE:
<223> OTHER INFORMATION: probe PREP-G
<220> FEATURE:
<221> NAME/KEY: misc_feature
<222> LOCATION: (3)..(3)
<223> OTHER INFORMATION: "n" is CNVK

<400> SEQUENCE: 9
ggnggggggg gggggg                                                    16

<210> SEQ ID NO 10
<211> LENGTH: 16
<212> TYPE: DNA
<213> ORGANISM: Artificial Sequence
<220> FEATURE:
<223> OTHER INFORMATION: probe PREP-AG
<220> FEATURE:
<221> NAME/KEY: misc_feature
<222> LOCATION: (3)..(3)
<223> OTHER INFORMATION: "n" is CNVK

<400> SEQUENCE: 10
agnagagaga gagaga                                                    16

<210> SEQ ID NO 11
<211> LENGTH: 18
<212> TYPE: DNA
```

```
<213> ORGANISM: Artificial Sequence
<220> FEATURE:
<223> OTHER INFORMATION: probe L861 AS
<220> FEATURE:
<221> NAME/KEY: misc_feature
<222> LOCATION: (15)..(15)
<223> OTHER INFORMATION: "n" is CNVK

<400> SEQUENCE: 11
ctcttccgca cccancag                                                 18

<210> SEQ ID NO 12
<211> LENGTH: 18
<212> TYPE: DNA
<213> ORGANISM: Artificial Sequence
<220> FEATURE:
<223> OTHER INFORMATION: probe L861 S
<220> FEATURE:
<221> NAME/KEY: misc_feature
<222> LOCATION: (14)..(14)
<223> OTHER INFORMATION: "n" is CNVK

<400> SEQUENCE: 12
ttgggctggc caanctgc                                                 18

<210> SEQ ID NO 13
<211> LENGTH: 16
<212> TYPE: DNA
<213> ORGANISM: Artificial Sequence
<220> FEATURE:
<223> OTHER INFORMATION: probe T790 AS
<220> FEATURE:
<221> NAME/KEY: misc_feature
<222> LOCATION: (4)..(4)
<223> OTHER INFORMATION: "n" is CNVK

<400> SEQUENCE: 13
tganctgcgt gatgag                                                   16

<210> SEQ ID NO 14
<211> LENGTH: 16
<212> TYPE: DNA
<213> ORGANISM: Artificial Sequence
<220> FEATURE:
<223> OTHER INFORMATION: probe T790 S
<220> FEATURE:
<221> NAME/KEY: misc_feature
<222> LOCATION: (3)..(3)
<223> OTHER INFORMATION: "n" is CNVK

<400> SEQUENCE: 14
canctcatca cgcagc                                                   16

<210> SEQ ID NO 15
<211> LENGTH: 15
<212> TYPE: DNA
<213> ORGANISM: Artificial Sequence
<220> FEATURE:
<223> OTHER INFORMATION: probe L858 AS
<220> FEATURE:
<221> NAME/KEY: misc_feature
<222> LOCATION: (3)..(3)
<223> OTHER INFORMATION: "n" is CNVK

<400> SEQUENCE: 15
cantttggcc agccc                                                    15

<210> SEQ ID NO 16
<211> LENGTH: 16
```

```
<212> TYPE: DNA
<213> ORGANISM: Artificial Sequence
<220> FEATURE:
<223> OTHER INFORMATION: probe L858 S
<220> FEATURE:
<221> NAME/KEY: misc_feature
<222> LOCATION: (3)..(3)
<223> OTHER INFORMATION: "n" is CNVK

<400> SEQUENCE: 16
cantttgggc tggcca                                               16

<210> SEQ ID NO 17
<211> LENGTH: 18
<212> TYPE: DNA
<213> ORGANISM: Homo sapiens

<400> SEQUENCE: 17
cagaagccta cgtgatgg                                             18

<210> SEQ ID NO 18
<211> LENGTH: 19
<212> TYPE: DNA
<213> ORGANISM: Homo sapiens

<400> SEQUENCE: 18
acctttgcga tctgcacac                                            19

<210> SEQ ID NO 19
<211> LENGTH: 190
<212> TYPE: DNA
<213> ORGANISM: Homo sapiens

<400> SEQUENCE: 19
cagaagccta cgtgatggcc agcgtggaca accccacgt gtgccgcctg ctgggcatct     60
gcctcacctc caccgtgcag ctcatcacgc agctcatgcc cttcggctgc ctcctggact   120
atgtccggga acacaaagac aatattggct cccagtacct gctcaactgg tgtgtgcaga   180
tcgcaaaggt                                                         190

<210> SEQ ID NO 20
<211> LENGTH: 13
<212> TYPE: DNA
<213> ORGANISM: Artificial Sequence
<220> FEATURE:
<223> OTHER INFORMATION: Total LNA probe
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (11)..(11)
<223> OTHER INFORMATION: LNA

<400> SEQUENCE: 20
cttcggctgc ctc                                                  13

<210> SEQ ID NO 21
<211> LENGTH: 190
<212> TYPE: DNA
<213> ORGANISM: Homo sapiens
```

<400> SEQUENCE: 21

```
cagaagccta cgtgatggcc agcgtggaca accccacgt gtgccgcctg ctgggcatct      60
gcctcacctc caccgtgcaa ctcatcatgc agctcatgcc cttcggctgc ctcctggact    120
atgtccggga acacaaagac aatattggct cccagtacct gctcaactgg tgtgtgcaga    180
tcgcaaaggt                                                           190
```

<210> SEQ ID NO 22
<211> LENGTH: 16
<212> TYPE: DNA
<213> ORGANISM: Artificial Sequence
<220> FEATURE:
<223> OTHER INFORMATION: probe PREPe.
<220> FEATURE:
<221> NAME/KEY: misc_feature
<222> LOCATION: (4)..(4)
<223> OTHER INFORMATION: "n" is CNVK

<400> SEQUENCE: 22

```
gcanccagca gtttgg                                                     16
```

<210> SEQ ID NO 23
<211> LENGTH: 16
<212> TYPE: DNA
<213> ORGANISM: Artificial Sequence
<220> FEATURE:
<223> OTHER INFORMATION: probe PREPf.
<220> FEATURE:
<221> NAME/KEY: misc_feature
<222> LOCATION: (4)..(4)
<223> OTHER INFORMATION: "n" is CNVK
<220> FEATURE:
<221> NAME/KEY: misc_feature
<222> LOCATION: (14)..(14)
<223> OTHER INFORMATION: i

<400> SEQUENCE: 23

```
gcanccagca gttngg                                                     16
```

<210> SEQ ID NO 24
<211> LENGTH: 16
<212> TYPE: DNA
<213> ORGANISM: Artificial Sequence
<220> FEATURE:
<223> OTHER INFORMATION: probe PREPg.
<220> FEATURE:
<221> NAME/KEY: misc_feature
<222> LOCATION: (4)..(4)
<223> OTHER INFORMATION: "n" is CNVK
<220> FEATURE:
<221> NAME/KEY: misc_feature
<222> LOCATION: (13)..(14)
<223> OTHER INFORMATION: i

<400> SEQUENCE: 24

```
gcanccagca gtnngg                                                     16
```

<210> SEQ ID NO 25
<211> LENGTH: 16
<212> TYPE: DNA
<213> ORGANISM: Artificial Sequence
<220> FEATURE:
<223> OTHER INFORMATION: probe PREPh.
<220> FEATURE:
<221> NAME/KEY: misc_feature
<222> LOCATION: (4)..(4)
<223> OTHER INFORMATION: "n" is CNVK
<220> FEATURE:
<221> NAME/KEY: misc_feature
<222> LOCATION: (12)..(14)
<223> OTHER INFORMATION: i

<400> SEQUENCE: 25
gcanccagca gnnngg                                                    16

<210> SEQ ID NO 26
<211> LENGTH: 20
<212> TYPE: DNA
<213> ORGANISM: Artificial Sequence
<220> FEATURE:
<223> OTHER INFORMATION: Total LNA probe
<220> FEATURE:
<221> NAME/KEY: misc_feature
<222> LOCATION: (9)..(9)
<223> OTHER INFORMATION: LNA
<220> FEATURE:
<221> NAME/KEY: misc_feature
<222> LOCATION: (14)..(14)
<223> OTHER INFORMATION: LNA

<400> SEQUENCE: 26
cagcatgtca agatcacaga                                                20

<210> SEQ ID NO 27
<211> LENGTH: 16
<212> TYPE: DNA
<213> ORGANISM: Artificial Sequence
<220> FEATURE:
<223> OTHER INFORMATION: probe L861 S
<220> FEATURE:
<221> NAME/KEY: misc_feature
<222> LOCATION: (4)..(4)
<223> OTHER INFORMATION: "n" is CNVK

<400> SEQUENCE: 27
ctgnccaaac tgctgg                                                    16

<210> SEQ ID NO 28
<211> LENGTH: 16
<212> TYPE: DNA
<213> ORGANISM: Artificial Sequence
<220> FEATURE:
<223> OTHER INFORMATION: probe L861 AS
<220> FEATURE:
<221> NAME/KEY: misc_feature
<222> LOCATION: (4)..(4)
<223> OTHER INFORMATION: "n" is CNVK
<220> FEATURE:
<221> NAME/KEY: misc_feature
<222> LOCATION: (13)..(13)
<223> OTHER INFORMATION: i

<400> SEQUENCE: 28
gcanccagca gtntgg                                                    16

<210> SEQ ID NO 29
<211> LENGTH: 16
<212> TYPE: DNA
<213> ORGANISM: Artificial Sequence
<220> FEATURE:
<223> OTHER INFORMATION: probe L861 S
<220> FEATURE:
<221> NAME/KEY: misc_feature
<222> LOCATION: (5)..(5)
<223> OTHER INFORMATION: "n" is CNVK
<220> FEATURE:
<221> NAME/KEY: misc_feature
<222> LOCATION: (14)..(14)
<223> OTHER INFORMATION: i

```
<400> SEQUENCE: 29
ccaanctgct gggngc                                                    16

<210> SEQ ID NO 30
<211> LENGTH: 20
<212> TYPE: DNA
<213> ORGANISM: Homo sapiens

<400> SEQUENCE: 30
gcatgaacta cttggaggac                                                20

<210> SEQ ID NO 31
<211> LENGTH: 20
<212> TYPE: DNA
<213> ORGANISM: Homo sapiens

<400> SEQUENCE: 31
acctaaagcc acctccttac                                                20

<210> SEQ ID NO 32
<211> LENGTH: 174
<212> TYPE: DNA
<213> ORGANISM: Homo sapiens

<400> SEQUENCE: 32
gcatgaacta cttggaggac cgtcgcttgg tgcaccgcga cctggcagcc aggaacgtac    60
tggtgaaaac accgcagcat gtcaagatca cagattttgg gctggccaaa ctgctgggtg   120
cggaagagaa agaataccat gcagaaggag gcaaagtaag gaggtggctt tggt         174
```

PHOTOCOUPLING METHOD USING PROBE CONTAINING PHOTORESPONSIVE NUCLEIC ACIDS

CROSS REFERENCE TO RELATED APPLICATIONS

This application is a national stage filing under section 371 of International Application No. PCT/JP2013/069694, filed on Jul. 19, 2013, and published on Jan. 23, 2014 as WO 2014/014106, which claims priority to Japanese Application No. 2012-161834, filed on Jul. 20, 2012, and to Japanese Application No. 2012-270614, filed on Dec. 11, 2012. The entire contents of each of said applications are hereby incorporated herein by reference.

SEQUENCE LISTING

This application contains a Sequence Listing, created on Dec. 1, 2014; the file, in ASCII format, is designated H0178302.txt and is 8.34KB in size. The file is hereby incorporated by reference in its entirety into the present application.

TECHNICAL FIELD

The present invention relates to a method for photocoupling with a probe comprising photo-responsive nucleotides.

BACKGROUND ART

In recent years, in order to establish personalized medicine, which is a of made-to-order treatment for individual patients, research has been proposed to reveal the relationship between specific gene polymorphisms of patients and drug sensitivity or drug response.

In particular, with advances in genome science, pharmacokinetics and polymorphisms of enzymes, proteins, and the like involved in drug response are being rapidly elucidated. In human genome analysis, single nucleotide polymorphisms (SNPs) are attracting attention as the most frequent polymorphism markers. The SNPs are already known to be useful in elucidating the relationship between various diseases and drug response. In addition, it is also known that a haplotype analysis using a plurality of SNPs is useful in analyzing disease susceptibility.

Especially in the medical field, a use in the diagnosis of disease prevalence using SNPs detection results, a use in the selection of an effective administration drug, a use in the prediction of side effects, and the like, are considered, and it is expected to lead to the improvement of QOL of patients as well as an increase in therapeutic effect. Many techniques have been reported for determining the bases of such SNPs sites, so-called typing. As a technique for typing single nucleotide polymorphism of DNA, a TaqMan PCR method, an Invader method, and the like, are known as techniques having high sequence selectivity enough to identify a single base substitution.

However, in the detection of acquired mutations as malignancies, since the wild-type nucleic acid molecule derived from normal cells, which are major components of a sample to be analyzed, is the background, it is often impossible to detect mutations such as a single base substitution with high sensitivity in the analysis methods as described above.

Therefore, as a particularly effective analysis technique as an alternative to the above methods, a use of photo-responsive nucleotides is disclosed. A photo-responsive nucleotide and a target nucleotide which are hybridized with each other can form photocoupling by carrying out photo-irradiation at a specific wavelength. This photocoupling occurs through the formation of an intermolecular covalent bond between the photo-responsive nucleotide molecule and the target nucleotide molecule, caused by a photoreaction of an artificial base moiety. The molecules photocoupled with each other in this way do not merely assemble with only a thermal stability, and thus, even if they are placed under conditions where a complementary duplex dissociates, the molecules do not dissociate and remain bound (Patent literature 1).

An analysis technique of detecting mutated genes using photo-responsive nucleotides is disclosed, based on the properties of the photo-responsive nucleotides, i.e., the findings that the photocoupling reaction proceeds very rapidly in about 1 second, and that the photocoupling does not occur if the hybridization is not complete (Patent literature 2).

Patent literatures 1 and 2 disclose the identification of SNPs using the photo-responsive nucleotides. However, they only disclose examples in which the use of the photo-responsive nucleotides is useful in selective amplification of mutated genes, based on the findings that photocoupling occurs when a probe containing the photo-responsive nucleotide is hybridized with a target site having a sequence complementary to the probe.

Therefore, in view of such conventional technical common knowledge, it has been considered that the photo-responsive nucleotide binds only with the target site having a complementary sequence, or a target nucleotide sequence in the vicinity of the target site, because it is necessary for the photocoupling that the probe containing the photo-responsive nucleotide should be hybridized with the target site having its complementary sequence, and the photocoupling is formed by the binding of the photo-responsive nucleotide with the target site, or the target nucleotide sequence in the vicinity of the target site.

CITATION LIST

Patent Literature

[Patent literature 1] JP 2009-254279 A
[Patent literature 2] WO 2012/033190

SUMMARY OF INVENTION

Technical Problem

The present inventors found that, in the reaction where a probe containing a photo-responsive nucleotide (i.e., a photocoupling probe) was photocoupled with a target nucleotide, the photocoupling proceeded only up to a certain percentage regardless of the amount of the target nucleotide, that is to say, the photocoupling stagnated. The present inventors conducted intensive studies based on the findings, and as a result, found that, as factors that stagnated the photocoupling, when the probe containing the photo-responsive nucleotide was photo-irradiated for the photocoupling with the target nucleotide, photocoupling in the self-sequence of the probe occurred. That is to say, it was presumed that since the photo-responsive nucleotide in the probe was assembled and photocoupled with a base capable of photocoupling with the photo-responsive nucleotide, a probe that could not hybridize with the target site and/or could not photocouple with the target nucleotide was accumulated depending on the photo-irradiation time (energy), and as a result, the photocoupling against the target nucleotide stagnated.

Additionally, in view of conventional, technical common knowledge, in the case where the amplification of a wild-type gene is selectively suppressed (amplification-suppressed), and a mutated gene is selectively amplified, the maximum advantage of the photo-coupling method using photo-responsive nucleotides, as disclosed in Patent literature 2, is the fact that the target nucleotide which has been once photocoupled by photo is not cleaved in the heat denaturing step of a PCR reaction step, that is to say, that the target nucleotide which has been once photocoupled by photo can be brought into a non-equilibrium system.

However, the present inventors found that even when it is photo-irradiated at a wavelength capable of photocoupling (365 nm), not only the probe was photocoupled with the target nucleotide, but also part of the probe which had been photocoupled with the target nucleotide was released through a photo-cleavage reaction, which does not naturally occur. That is to say, it was considered that the light equilibrium state in which the photocoupling reaction and the photocoupling-cleaving reaction concurrently occurred was a factor that stagnated the photocoupling against the target nucleotide.

An object of the present invention is to solve the problem that the photocoupling with a target nucleotide using a probe containing photo-responsive nucleotides stagnates, and to provide a method of improving photocoupling efficiency, and a kit thereof.

Solution to Problem

The present inventors intensively studied the means for solving the problem, and as a result, found that in order to avoid the stagnation of the photocoupling efficiency, the effective concentration of the probe containing the photo-responsive nucleotide was maintained in a reaction solution by suppressing photocoupling in the self-sequence of the probe, and that hybridization could be promoted and the photocoupling efficiency could be improved by increasing the substantial concentration of the probe containing the photo-responsive nucleotide, locally around the target site.

The present invention relates to:

[1] a photocoupling method, characterized by hybridizing a target site present in a nucleic acid sample with a first probe having a sequence complementary to the target site and containing a photo-responsive nucleotide, in a reaction solution, and carrying out photocoupling by photo-irradiation, wherein self-assembly caused by the photo-responsive nucleotide contained in the first probe is suppressed,

[2] the photocoupling method of [1], characterized in that the self-assembly caused by the photo-responsive nucleotide contained in the first probe is suppressed by co-existing with a second probe being highly complementary to the first probe,

[3] the photocoupling method of [1] or [2], wherein being highly complementary means a state in which the first probe and the second probe are complementary to one another, and a base to be photocoupled with the photo-responsive nucleotide itself in the first probe under predetermined photocoupling conditions hybridizes with the second probe,

[4] the photocoupling method of any one of [1] to [3], wherein a target nucleotide contained in the target site present in the nucleic acid sample is photocoupled with the photo-responsive nucleotide contained in the first probe,

[5] the photocoupling method of any one of [1] to [4], wherein the second probe contains a photo-responsive nucleotide,

[6] the photocoupling method of any one of [1] to [5], wherein the first probe and the second probe contain photo-responsive nucleotides, and a third probe having a sequence complementary to the first probe and/or the second probe is used so that the photo-responsive nucleotide or the photo-responsive nucleotides present in the first probe and/or the second probe cannot be photocoupled itself in a non-complementary region between the first probe and the second probe,

[7] the photocoupling method of [1], characterized by hybridizing a target site present in a nucleic acid sample, a first probe having a sequence complementary to the target site and containing a photo-responsive nucleotide, and a fourth probe having a sequence complementary to the target site and containing a target nucleotide, so that they are placed adjacent in a reaction solution, and carrying out photocoupling by photo-irradiation between the target nucleotide contained in the fourth probe and the photo-responsive nucleotide contained in the first probe, wherein photocoupling of the first probe itself is suppressed by co-existing with a second probe being highly complementary to the first probe,

[8] the photocoupling method of any one of [1] to [7], characterized by using the first probe in which a nucleotide that self-assembles with the photo-responsive nucleotide in the first probe is substituted with a nucleotide not capable of photocoupling with the photo-responsive nucleotide, and characterized in that photocoupling of the first probe itself is suppressed,

[9] the photocoupling method of [8], wherein the nucleotide not capable of photocoupling with the photo-responsive nucleotide is a purine base,

[10] the photocoupling method of [8], wherein the nucleotide not capable of photocoupling with the photo-responsive nucleotide is a synthetic base obtained by artificially converting a pyrimidine ring,

[11] the photocoupling method of any one of [1] to [10], wherein an anionic substance is contained in the reaction solution,

[12] the photocoupling method of any one of [1] to [11], characterized in that at least one photocoupling probe is contained at a concentration of 0.1 μmol/L or more in the reaction solution,

[13] A method for gene analysis, using the photocoupling method of any one of [1] to [12],

[14] the method for gene analysis of [13], which is a method for gene detection or a method for nucleic acid amplification,

[15] a method for mutated nucleic acid detection, characterized in that the method for nucleic acid amplification described in claim 14 is a method for detecting the presence or absence of the mutated nucleic acid, by selectively amplifying a nucleotide sequence for amplification containing a target site of the mutated nucleic acid,

[16] a photocoupling kit, characterized by comprising a first probe having a sequence complementary to a target site present in a nucleic acid sample, and containing a photo-responsive nucleotide, and a second probe being highly complementary to the first probe,

[17] the photocoupling kit of [16], wherein the first probe is capable of photocoupling with a target nucleotide contained in the target site present in the nucleic acid sample,

[18] the photocoupling kit of [16], further comprising a fourth probe containing a target nucleotide capable of photocoupling with the photo-responsive nucleotide contained in the first probe,

[19] the photocoupling kit of any one of [16] to [18], wherein the second probe contains a photo-responsive nucleotide, and

[20] the photocoupling kit of any one of [16] to [19], wherein the first probe is a probe in which a nucleotide that self-assembles with the photo-responsive nucleotide in the first probe is substituted with a nucleotide not capable of photocoupling with the photo-responsive nucleotide.

Advantageous Effects of Invention

According to the present invention, in a gene analysis method using photo-responsive nucleotides, the photocoupling efficiency between the target site and a probe containing the photo-responsive nucleotide can be improved. That is to say, the present invention is effective in a gene analysis method that requires high sensitivity and high specificity, because photocoupling against the target nucleotide can be specifically and effectively carried out.

DESCRIPTION OF EMBODIMENTS

Figure 1:
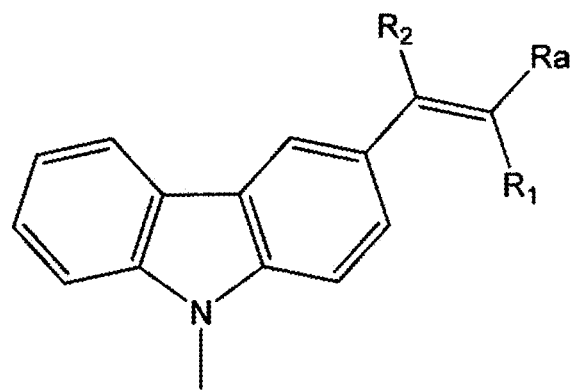
FIG. 1 is the structural formula of 3-cyanovinylcarbazole (CNVK), as an example of photo-responsive nucleotides.
Figure 2:
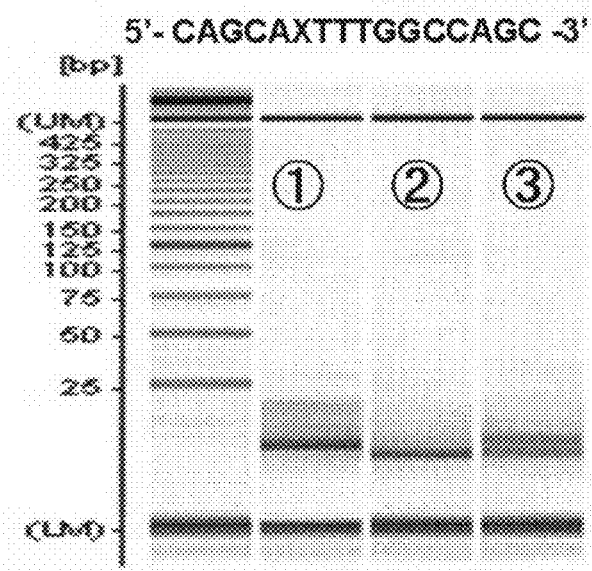
FIG. 2 is a result obtained by carrying out photo-irradiation at a photocoupling-forming wavelength followed by photo-irradiation at a photocoupling-cleaving wavelength, with respect to a photocoupling probe, which was designed so that part of the exon 21 (ex.21) region of an EGFR gene was the photocoupling forming target, and the CNVK as photo-responsive nucleotides was introduced into a position close to the 5' terminus, and confirming the resulting sample by electrophoresis.
Figure 3:
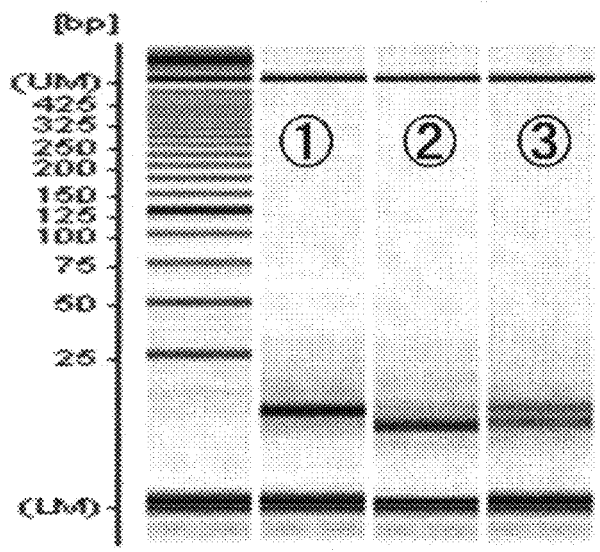
FIG. 3 is a result obtained by carrying out photo-irradiation at a photocoupling-forming wavelength followed by photo-irradiation at a photocoupling-cleaving wavelength, with respect to a photocoupling probe, which was designed so that part of the exon 21 (ex.21) region of an EGFR gene was the photocoupling forming target, and the CNVK as photo-responsive nucleotides was introduced into a position closer to the center than the 5' terminus, and confirming the resulting sample by electrophoresis.
Figure 4:
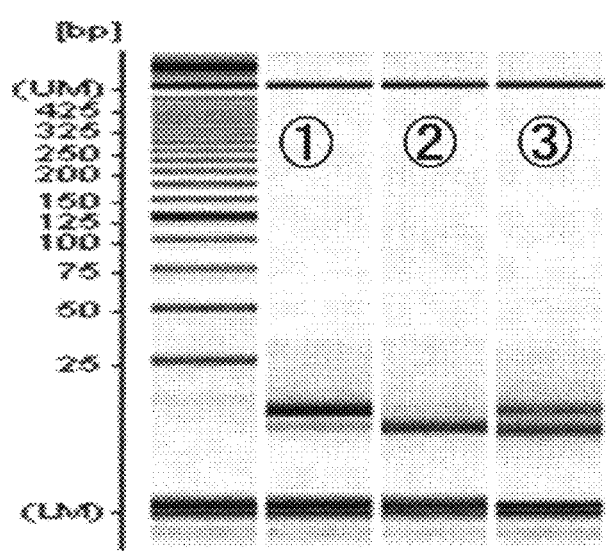
FIG. 4 is a result obtained by carrying out photo-irradiation at a photocoupling-forming wavelength followed by photo-irradiation at a photocoupling-cleaving wavelength, with respect to a photocoupling probe, which was designed so that part of the exon 21 (ex.21) region of an EGFR gene was the photocoupling forming target, and the CNVK as photo-responsive nucleotides was introduced into a position closer to the center than the 3' terminus, and confirming the resulting sample by electrophoresis.
Figure 5:
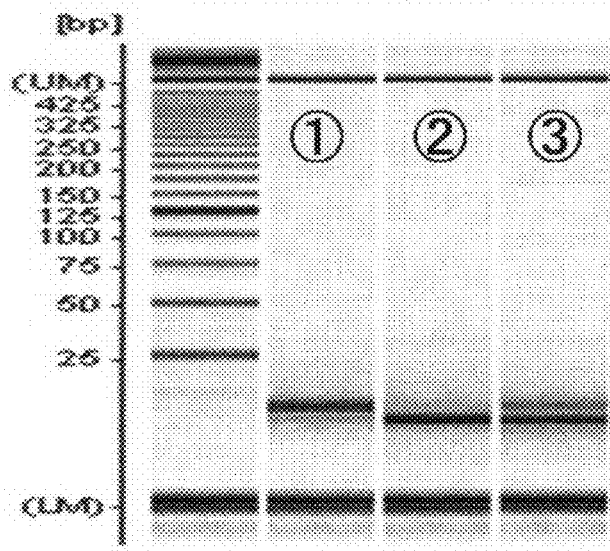
FIG. 5 is a result obtained by carrying out photo-irradiation at a photocoupling-forming wavelength followed by photo-irradiation at a photocoupling-cleaving wavelength, with respect to a photocoupling probe, which was designed so that part of the exon 21 (ex.21) region of an EGFR gene was the photocoupling forming target, and the CNVK as photo-responsive nucleotides was introduced into a position close to the 3' terminus, and confirming the resulting sample by electrophoresis.

Hereinafter embodiments of the present invention will be explained in detail with reference to the drawings, but utilization methods and kit embodiments are not limited to the following embodiments.

The definitions of the terms as used herein, such as DNA, RNA, gene expression, code, template, promoter, primer, PCR, and sequence, are the same as those currently and commonly used in molecular biology, genetics, genetic engineering, and the like.

The term "nucleic acid" as used herein is not limited, so long as it is DNA or RNA, or the nucleic acid analogues described below. The nucleic acid may be a naturally-occurring compound or a synthetic compound. Examples of the naturally-occurring nucleic acid include genomic DNA, mRNA, tRNA, rRNA, and hnRNA, which are collected from organisms. Examples of the synthetic nucleic acid include DNA synthesized by a known chemical synthesis method such as a β-cyanoethylphosphoramidite method or a DNA solid-phase synthesis method, nucleic acid synthesized by a known nucleic acid amplification method such as PCR, and cDNA synthesized by a reverse-transcriptional reaction.

The term "nucleic acid sample" as used herein is not limited, so long as it is a sample containing nucleic acid and suspected of comprising a target site. It is, for example, a sample suspected of containing at least one of a wild-type nucleic acid having a target site and its mutated nucleic acid, and preferably a sample suspected of containing both nucleic acids. Examples of the nucleic acid sample include genomic DNA or RNA obtained from whole cells contained in a sample such as blood or tissues. Nucleic acid can be extracted from a sample by a conventional method such as a phenol/chloroform method. In connection with this, the percentage of presence of the mutated nucleic acid in the nucleic acid sample is not limited. For example, it may be 100% of a wild-type nucleic acid, or 50% of a wild-type nucleic acid and 50% of a mutated nucleic acid. The nucleic acid sample may be genomic DNA obtained from cells, mRNAs prepared from cells, or cDNAs obtained by a reverse-transcription reaction using mRNAs as a template. Further, the nucleic acid sample may be an artificial mixture of a number of cloned genes, nucleic acid artificially amplified by a nucleic acid amplification method, or a mixture thereof.

The term "wild-type nucleic acid" as used herein means a nucleic acid prior to mutation, typically, a nucleic acid which has no mutations and contains genetic information having its original normal functions. The term "genetic information" as used herein includes not only a transcriptional region which encodes information of mRNA, tRNA, rRNA, snRNA, and the like, but also a regulatory region such as a promoter which is required for gene expression.

The term "mutated nucleic acid" as used herein means a nucleic acid in which a mutation has occurred. The term "mutation" as used herein means a change in the sequence of a nucleic acid such as DNA and RNA, and includes a base substitution, insertion, deletion, inversion, duplication, translocation, and the like used in genetics and the like. The region of the mutation in a mutated nucleic acid is not limited to a transcriptional region, but includes a regulatory region such as a promoter which is required for gene expression. In this regard, the mutation in a mutated nucleic acid does not require a functional change. The "mutation" includes congenital and acquired mutations.

The term "target site" as used herein means a site to which a probe hybridizes in a nucleotide sequence present in a nucleic acid sample. The hybridizing probe is not needed to contain a photo-responsive nucleotide. The hybridization between the nucleotide sequence and the probe means that the probe hybridizes to the full-length or part of the nucleotide sequence. The term "target nucleotide" as used herein means a site containing a nucleotide sequence which a photo-responsive nucleotide binds to, and photocouples with. The term "photocoupling" as used herein means that a probe containing a photo-responsive nucleotide covalently binds to a target nucleotide. It is known that there is a plurality of types of covalent bonds formed, depending on the type of the photo-responsive nucleotide, and the type of covalent bond is not limited. More particularly, both a case where a crosslinking-type covalent bond is formed, and a case where a ligation-type is formed may be included in the present invention.

The photo-responsive nucleotide is not limited, so long as it has properties to react with light and to be coupled with another nucleotide by forming a covalent bond. For example, nucleotides of formulae I to VII described below may be used. The photo-responsive nucleotides of formulae I to VII described below can covalently bind to a pyrimidine base. It is not limited, so long as it can covalently bind to the photo-responsive nucleotides. As a base which forms a carbon-carbon double bond, when it is a naturally-occurring substance, preferably, a sequence containing cytosine, thymine, uracil, or the like may be a target nucleotide. The target nucleotide may exist in the target site, or may be designed so that it exists in a probe other than the photocoupling probe used in the present invention.

The term "objective site" as used herein means a site where a base with mutation exists in a mutated nucleic acid, and a site to be analyzed, including a wild-type nucleic acid, by the gene analysis method in the present invention. For example, when a base substitution has occurred, the objective site corresponds to the substituted base in both a wild-type nucleic acid and a mutated nucleic acid. When an insertion has occurred, the objective site corresponds to the inserted base in a mutated nucleic acid, and corresponds to the site into which the base has been inserted in the mutated nucleic acid, in a wild-type nucleic acid. When a deletion has occurred, the objective site corresponds to the site from which the base is deleted in a mutated nucleic acid, and corresponds to the base deleted in the mutated nucleic acid, in a wild-type nucleic acid. The objective site may be a final subject to be analyzed in the present invention. For example, the objective site may be a strand having a sequence encoding genetic information (hereinafter referred to as a sense strand), or a strand having a sequence complementary to the sense strand (hereinafter referred to as an antisense strand). The objective site may include a change in a nucleotide sequence in a sequence that is not directly involved in genetic information.

The nucleotide sequence of the photo-coupling probe, and the positions and numbers of the photo-responsive nucleotides are not limited, so long as they can specifically hybridize with part or all of the target site.

Depending on conditions, such as a mutated position, the kind of a base, and the length of the photo-coupling probe, the photo-coupling probe may be designed so that the target site coincides with the objective site, or so that the target site is set at a site different from the objective site. When the target site coincides with the objective site, part of the site may be overlapped, or the whole site may be overlapped.

The photo-responsive nucleotide which may be used in the present invention is not limited, so long as it can be coupled with the target nucleotide by photo-irradiation.

For example, psoralen derivatives (Chang, E. et al. Biochemistry 1991, 30, 8283), aminopurine derivatives (JP 2001-206896 A), or 4-thiouracil may be used. Since the psoralen derivatives have properties that specifically react with thymine in the nucleotide sequence 5'-AT-3', and the aminopurine derivatives are not sequence-dependent, but are cytidine-specific, the application of these derivatives is limited, and therefore, the following photo-responsive nucleotides without such limitations are preferable.

The first preferable photo-responsive nucleotides are ones having, as the base moiety, the group of the formula I:

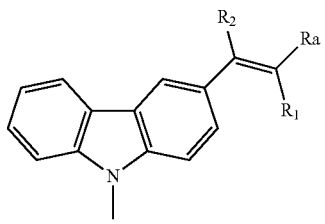

[Chem. 1]

wherein Ra is a cyano group, an amide group, a carboxyl group, a $C_2$-$C_7$ alkoxycarbonyl group, or a hydrogen atom, and $R_1$ and $R_2$ are independently a cyano group, an amide group, a carboxyl group, a $C_2$-$C_7$ alkoxycarbonyl group, or a hydrogen atom (Org. Lett., Vol. 10, No. 15, 2008, JP 2009-254279 A). In the case where a nucleic acid attached thereto is DNA, the substituted carbazolyl group of the formula I is linked to the carbon atom (C) at the 1-position of 2-deoxyribose at the P-position, as shown in the formula I(a):

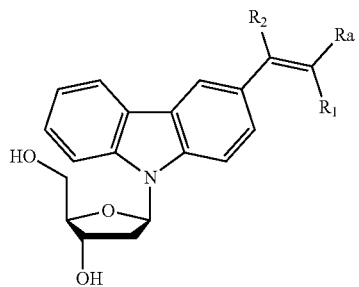

[Chem. 2]

Concrete examples of the first photo-responsive nucleotides include 3-cyanovinylcarbazole-1'-β-deoxyriboside ($^{CNV}$K).

The second preferable photo-responsive nucleotides are ones having the group of the formula II:

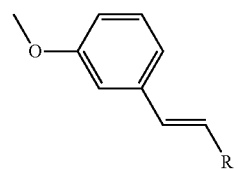

[Chem. 3]

wherein R is —CN, —CONR$^1$R$^2$, or —COOR$^3$, R$^1$ to R$^3$ are independently a hydrogen atom or an alkyl group $C_nH_{2n+1}$ (n≥1), and the upper limit of n is not limited, but may be, for example, 1 to 7, preferably 1 to 5 (Organic & Biomolecular Chemistry 2007, 5, 2583, Bioorganic & Medicinal Chemistry Letters 15 (2005) 1299-1301, and JP 2005-348645 A). In the case where a nucleic acid attached thereto is DNA, the substituted phenoxy group of the formula II is linked to the carbon atom (C) at the 1-position of 2-deoxyribose at the α-position, as shown in the formula II(a):

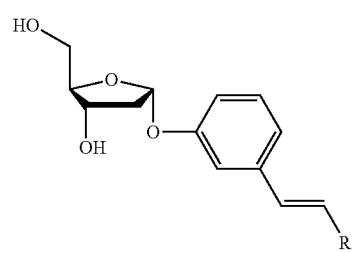

[Chem. 4]

R is preferably —CN, —COOH, or —COOMe, and more preferably —COOH or —COOMe.

The groups of the formula I and formula II impart photo-coupling properties to the nucleic acid. The photo-coupling properties may be imparted to DNA and RNA as well as nucleotide analogues. These photo-responsive nucleotides may be prepared in a fashion similar to a conventional method of producing nucleic acid.

In a preferred embodiment of the present invention, the photo-responsive nucleotides have, as the base moiety, the group of formula III:

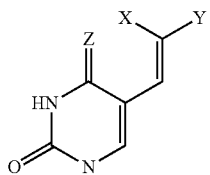

[Chem. 5]

wherein Z represents O or NH; at least one of X and Y represents an electron-withdrawing group selected from the group consisting of a carboxyl group, a lower alkoxycarbonyl group, a substituted amide group and a cyano group; and the residue of X and Y represents a hydrogen atom. The alkyl group in the alkoxycarbonyl group may be exemplified by a lower alkyl group having 1 to 10 carbon atoms, preferably 1 to 5 carbon atoms. Both of the substituents X and Y may be identical or different electron-withdrawing groups at the same time. Alternatively, only one of the substituents X and Y may be an electron-withdrawing group, while the other may be a hydrogen atom. In Formula III, it is preferable that Z is O; X is a hydrogen atom; and Y is a carboxyl group, a lower alkoxycarbonyl group, a substituted amide group or a cyano group. As a particularly preferred base moiety, 5-vinyl-2'-deoxyuridine and 5-carboxyvinyl-2'-deoxyuridine may be mentioned. 5-Carboxyvinyl-2'-deoxyuridine is particularly preferred.

In another preferred embodiment, the photo-responsive nucleotides have, as the base moiety, the group of formula IV:

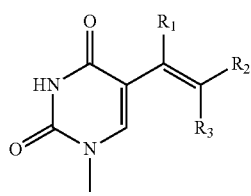

[Chem. 6]

wherein $R_1$ is a hydrogen atom; at least one of $R_2$ and $R_3$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_2$ and $R_3$ represents a hydrogen atom or a cyano group.

At least one of $R_2$ and $R_3$ is preferably a carboxyl group, while a combination of a carboxyl group and a hydrogen atom is preferred as the combination of $R_2$ and $R_3$.

At least one of $R_2$ and $R_3$ is preferably a lower alkoxycarbonyl group, and the alkyl moiety in the lower alkoxycarbonyl group may be exemplified by lower alkyl having 1 to 10 carbon atoms, preferably 1 to 5 carbon atoms, more preferably 1 to 3 carbon atoms, even more preferably 1 to 2 carbon atoms, and particularly preferably one carbon atom. That is, preferred examples of the lower alkoxycarbonyl group include a methoxycarbonyl group, an ethoxycarbonyl group, a propoxycarbonyl group, a butoxycarbonyl group and the like. A methoxycarbonyl group, an ethoxycarbonyl group and a propoxycarbonyl group are more preferred; a methoxycarbonyl group and an ethoxycarbonyl group are even more preferred; and a methoxycarbonyl group is particularly preferred. A combination of a lower alkoxycarbonyl group and a hydrogen atom, particularly a combination of a methoxycarbonyl group and a hydrogen atom are preferred as the combination of $R_2$ and $R_3$.

At least one of $R_2$ and $R_3$ is preferably a lower alkenyl group, and the lower alkenyl group may be exemplified by a lower alkenyl group having 2 to 10 carbon atoms, preferably 2 to 5 carbon atoms, more preferably 2 to 3 carbon atoms, and particularly preferably 2 carbon atoms. A combination of a lower alkenyl group and a hydrogen atom, particularly a combination of a vinyl group and a hydrogen atom are preferred as the combination of $R_2$ and $R_3$.

At least one of $R_2$ and $R_3$ is preferably a lower alkynyl group, and the lower alkynyl group may be exemplified by a lower alkynyl group having 2 to 10 carbon atoms, preferably 2 to 5 carbon atoms, more preferably 2 to 3 carbon atoms, and particularly preferably 2 carbon atoms. A combination of a lower alkynyl group and a hydrogen atom, particularly a combination of an ethynyl group and a hydrogen atom are preferred as the combination of $R_2$ and $R_3$.

At least one of $R_2$ and $R_3$ is preferably substituted amide, and the substituted amide may be exemplified by mono-substituted, N-substituted amide. Preferred examples thereof include N-alkylamide and N-aminoalkylamide. Such N-alkylamide or N-aminoalkylamide is preferably a compound having 1 to 10 carbon atoms, preferably 1 to 5 carbon atoms, more preferably 1 to 3 carbon atoms, and particularly preferably 3 carbon atoms, and N-aminoalkylamide is particularly preferred. A combination of substituted amide and a hydrogen atom, particularly a combination of N-amino (C1-C3 alkyl)amide and a hydrogen atom are preferred as the combination of $R_2$ and $R_3$.

At least one of $R_2$ and $R_3$ is preferably an amide group, and a combination of an amide group and a hydrogen atom is preferred as the combination of $R_2$ and $R_3$. At least one of $R_2$ and $R_3$ is preferably a cyano group, and a combination of a cyano group and a cyano group, and a combination of a cyano group and a hydrogen atom are preferred as the combination of $R_2$ and $R_3$.

At least one of $R_2$ and $R_3$ is preferably a hydrogen atom, and a combination including at least one hydrogen atom, and a combination of a hydrogen atom and a hydrogen atom are preferred as the combination of $R_2$ and $R_3$.

In still another preferred embodiment, the photo-responsive nucleotides have, as the base moiety, the group of formula V:

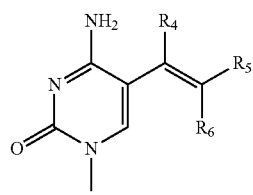

[Chem. 7]

wherein $R_4$ is a hydrogen atom or a lower alkyl group; at least one of $R_5$ and $R_6$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_5$ and $R_6$ represents a hydrogen atom or a cyano group.

$R_4$ is particularly preferably a hydrogen atom.

$R_4$ is preferably a lower alkyl group, and the lower alkyl group is a group having 1 to 5 carbon atoms, preferably 1 to 3 carbon atoms, more preferably 1 to 2 carbon atoms, and particularly preferably one carbon atom. Such lower alkyl group may be exemplified by a methyl group, an ethyl group, a propyl group or the like, and a methyl group and an ethyl group are preferred, while a methyl group is particularly preferred.

At least one of $R_5$ and $R_6$ is preferably a carboxyl group, and a combination of a carboxyl group and a hydrogen atom is preferred as the combination of $R_5$ and $R_6$.

At least one of $R_5$ and $R_6$ is preferably a lower alkoxycarbonyl group, and the alkyl moiety in the lower alkoxycarbonyl group may be exemplified by lower alkyl having 1 to 10 carbon atoms, preferably 1 to 5 carbon atoms, more preferably 1 to 3 carbon atoms, even more preferably 1 to 2 carbon atoms, and particularly preferably one carbon atom. That is, preferred examples of the lower alkoxycarbonyl group include a methoxycarbonyl group, an ethoxycarbonyl group, a propoxycarbonyl group, a butoxycarbonyl group and the like. A methoxycarbonyl group, an ethoxycarbonyl group and a propoxycarbonyl group are more preferred; a methoxycarbonyl group and an ethoxycarbonyl group are even more preferred; and a methoxycarbonyl group is particularly preferred. A combination of a lower alkoxycarbonyl group and a hydrogen atom, particularly a combination of a methoxycarbonyl group and a hydrogen atom are preferred as the combination of $R_5$ and $R_6$.

At least one of $R_5$ and $R_6$ is preferably a lower alkenyl group, and the lower alkenyl group may be exemplified by a lower alkenyl group having 2 to 10 carbon atoms, preferably 2 to 5 carbon atoms, more preferably 2 to 3 carbon atoms, and particularly preferably 2 carbon atoms. A combination of a lower alkenyl group and a hydrogen atom, particularly a combination of a vinyl group and a hydrogen atom are preferred as the combination of $R_5$ and $R_6$.

At least one of $R_5$ and $R_6$ is preferably a lower alkynyl group, and the lower alkynyl group may be exemplified by a lower alkynyl group having 2 to 10 carbon atoms, preferably 2 to 5 carbon atoms, more preferably 2 to 3 carbon atoms, and particularly preferably 2 carbon atoms. A combination of a lower alkynyl group and a hydrogen atom, particularly a combination of an ethynyl group and a hydrogen atom are preferred as the combination of $R_5$ and $R_6$.

At least one of $R_5$ and $R_6$ is preferably substituted amide, and the substituted amide may be exemplified by mono-substituted, N-substituted amide. Preferred examples thereof include N-alkylamide and N-aminoalkylamide. Such N-alkylamide or N-aminoalkylamide is preferably a compound having 1 to 10 carbon atoms, preferably 1 to 5 carbon atoms, more preferably 1 to 3 carbon atoms, and particularly preferably 3 carbon atoms, and N-aminoalkylamide is particularly preferred. A combination of substituted amide and a hydrogen atom, particularly a combination of N-amino(C1-C3 alkyl)amide and a hydrogen atom are preferred as the combination of $R_5$ and $R_6$.

At least one of $R_5$ and $R_6$ is preferably an amide group, and a combination of an amide group and a hydrogen atom is preferred as the combination of $R_5$ and $R_6$.

At least one of $R_5$ and $R_6$ is preferably a cyano group, and a combination of a cyano group and a cyano group, and a combination of a cyano group and a hydrogen atom are preferred as the combination of $R_5$ and $R_6$.

At least one of $R_5$ and $R_6$ is preferably a hydrogen atom, and a combination including at least one hydrogen atom, and a combination of a hydrogen atom and a hydrogen atom are preferred as the combination of $R_5$ and $R_6$.

In still another preferred embodiment, the photo-responsive nucleotides have, as the base moiety, the group of formula VI:

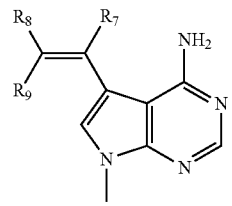

[Chem. 8]

wherein $R_7$ is a hydrogen atom or a lower alkyl group; at least one of $R_8$ and $R_9$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_8$ and $R_9$ represents a hydrogen atom or a cyano group.

R7 is particularly preferably a hydrogen atom.

R7 is preferably a lower alkyl group, and the lower alkyl group is a group having 1 to 5 carbon atoms, preferably 1 to 3 carbon atoms, more preferably 1 to 2 carbon atoms, and particularly preferably one carbon atom. Such lower alkyl group may be exemplified by a methyl group, an ethyl group, a propyl group or the like, and a methyl group and an ethyl group are preferred, while a methyl group is particularly preferred.

At least one of $R_8$ and $R_9$ is preferably a carboxyl group, and a combination of a carboxyl group and a hydrogen atom is preferred as the combination of $R_8$ and $R_9$.

At least one of $R_8$ and $R_9$ is preferably a lower alkoxycarbonyl group, and the alkyl moiety in the lower alkoxycarbonyl group may be exemplified by lower alkyl having 1 to 10 carbon atoms, preferably 1 to 5 carbon atoms, more preferably 1 to 3 carbon atoms, even more preferably 1 to 2 carbon atoms, and particularly preferably one carbon atom. That is, preferred examples of the lower alkoxycarbonyl group include a methoxycarbonyl group, an ethoxycarbonyl group, a propoxycarbonyl group, a butoxycarbonyl group and the like. A methoxycarbonyl group, an ethoxycarbonyl group and a propoxycarbonyl group are more preferred; a methoxycarbonyl group and an ethoxycarbonyl group are even more preferred; and a methoxycarbonyl group is particularly preferred. A combination of a lower alkoxycarbonyl group and a hydrogen atom, particularly a combination of a methoxycarbonyl group and a hydrogen atom are preferred as the combination of $R_8$ and $R_9$.

At least one of $R_8$ and $R_9$ is preferably a lower alkenyl group, and the lower alkenyl group may be exemplified by a lower alkenyl group having 2 to 10 carbon atoms, preferably 2 to 5 carbon atoms, more preferably 2 to 3 carbon atoms, and particularly preferably 2 carbon atoms. A combination of a lower alkenyl group and a hydrogen atom, particularly a combination of a vinyl group and a hydrogen atom are preferred as the combination of $R_8$ and $R_9$.

At least one of $R_8$ and $R_9$ is preferably a lower alkynyl group, and the lower alkynyl group may be exemplified by a lower alkynyl group having 2 to 10 carbon atoms, preferably 2 to 5 carbon atoms, more preferably 2 to 3 carbon atoms, and particularly preferably 2 carbon atoms. A combination of a lower alkynyl group and a hydrogen atom, particularly a combination of an ethynyl group and a hydrogen atom are preferred as the combination of $R_8$ and $R_9$.

At least one of $R_8$ and $R_9$ is preferably substituted amide, and the substituted amide may be exemplified by mono-substituted, N-substituted amide. Preferred examples thereof include N-alkylamide and N-aminoalkylamide. Such N-alkylamide or N-aminoalkylamide is preferably a compound having 1 to 10 carbon atoms, preferably 1 to 5 carbon atoms, more preferably 1 to 3 carbon atoms, and particularly preferably 3 carbon atoms, and N-aminoalkylamide is particularly preferred. A combination of substituted amide and a hydrogen atom, particularly a combination of N-amino (C1-C3 alkyl)amide and a hydrogen atom are preferred as the combination of $R_8$ and $R_9$.

At least one of $R_8$ and $R_9$ is preferably an amide group, and a combination of an amide group and a hydrogen atom is preferred as the combination of $R_8$ and $R_9$.

At least one of $R_8$ and $R_9$ is preferably a cyano group, and a combination of a cyano group and a cyano group, and a combination of a cyano group and a hydrogen atom are preferred as the combination of $R_8$ and $R_9$.

At least one of $R_8$ and $R_9$ is preferably a hydrogen atom, and a combination including at least one hydrogen atom, and a combination of a hydrogen atom and a hydrogen atom are preferred as the combination of $R_8$ and $R_9$.

In still another preferred embodiment, the photo-responsive nucleotides have, as the base moiety, the group of formula VII:

[Chem. 9]

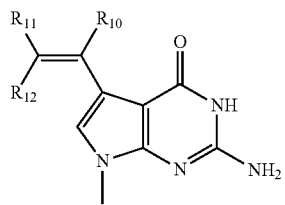

wherein $R_{10}$ is a hydrogen atom or a lower alkyl group; at least one of $R_{11}$ and $R_{12}$ represents a group selected from the group consisting of a carboxyl group, a lower alkoxycarbonyl group, a lower alkenyl group, a lower alkynyl group, a substituted amide group, an amide group, a cyano group and a hydrogen atom; and the residue of $R_{11}$ and $R_{12}$ represents a hydrogen atom or a cyano group; as a base moiety.

$R_{10}$ is particularly preferably a hydrogen atom.

$R_{10}$ is preferably a lower alkyl group, and the lower alkyl group is a group having 1 to 5 carbon atoms, preferably 1 to 3 carbon atoms, more preferably 1 to 2 carbon atoms, and particularly preferably one carbon atom. Such lower alkyl group may be exemplified by a methyl group, an ethyl group, a propyl group or the like, and a methyl group and an ethyl group are preferred, while a methyl group is particularly preferred.

At least one of $R_{11}$ and $R_{12}$ is preferably a carboxyl group, and a combination of a carboxyl group and a hydrogen atom is preferred as the combination of $R_{11}$ and $R_{12}$.

At least one of $R_{11}$ and $R_{12}$ is preferably a lower alkoxycarbonyl group, and the alkyl moiety in the lower alkoxycarbonyl group may be exemplified by lower alkyl having 1 to 10 carbon atoms, preferably 1 to 5 carbon atoms, more preferably 1 to 3 carbon atoms, even more preferably 1 to 2 carbon atoms, and particularly preferably one carbon atom. That is, preferred examples of the lower alkoxycarbonyl group include a methoxycarbonyl group, an ethoxycarbonyl group, a propoxycarbonyl group, a butoxycarbonyl group and the like. A methoxycarbonyl group, an ethoxycarbonyl group and a propoxycarbonyl group are more preferred; a methoxycarbonyl group and an ethoxycarbonyl group are even more preferred; and a methoxycarbonyl group is particularly preferred. A combination of a lower alkoxycarbonyl group and a hydrogen atom, particularly a combination of a methoxycarbonyl group and a hydrogen atom are preferred as the combination of $R_{11}$ and $R_{12}$.

At least one of $R_{11}$ and $R_{12}$ is preferably a lower alkenyl group, and the lower alkenyl group may be exemplified by a lower alkenyl group having 2 to 10 carbon atoms, preferably 2 to 5 carbon atoms, more preferably 2 to 3 carbon atoms, and particularly preferably 2 carbon atoms. A combination of a lower alkenyl group and a hydrogen atom, particularly a combination of a vinyl group and a hydrogen atom are preferred as the combination of $R_{11}$ and $R_{12}$.

At least one of $R_{11}$ and $R_{12}$ is preferably a lower alkynyl group, and the lower alkynyl group may be exemplified by a lower alkynyl group having 2 to 10 carbon atoms, preferably 2 to 5 carbon atoms, more preferably 2 to 3 carbon atoms, and particularly preferably 2 carbon atoms. A combination of a lower alkynyl group and a hydrogen atom, particularly a combination of an ethynyl group and a hydrogen atom are preferred as the combination of $R_{11}$ and $R_{12}$.

At least one of $R_{11}$ and $R_{12}$ is preferably substituted amide, and the substituted amide may be exemplified by mono-substituted, N-substituted amide. Preferred examples thereof include N-alkylamide and N-aminoalkylamide. Such N-alkylamide or N-aminoalkylamide is preferably a compound having 1 to 10 carbon atoms, preferably 1 to 5 carbon atoms, more preferably 1 to 3 carbon atoms, and particularly preferably 3 carbon atoms, and N-aminoalkylamide is particularly preferred. A combination of substituted amide and a hydrogen atom, and particularly a combination of N-amino (C1-C3 alkyl)amide and a hydrogen atom, are preferred as the combination of $R_{11}$ and $R_{12}$.

At least one of $R_{11}$ and $R_{12}$ is preferably an amide group, and a combination of an amide group and a hydrogen atom is preferred as the combination of $R_{11}$ and $R_{12}$.

At least one of $R_{11}$ and $R_{12}$ is preferably a cyano group, and a combination of a cyano group and a cyano group, and a combination of a cyano group and a hydrogen atom are preferred as the combination of $R_{11}$ and $R_{12}$.

At least one of $R_{11}$ and $R_{12}$ is preferably a hydrogen atom, and a combination including at least one hydrogen atom, and a combination of a hydrogen atom and a hydrogen atom are preferred as the combination of $R_{11}$ and $R_{12}$.

Suitable structural formulae of such bases are illustrated as follows. However, the bases that can be used in the present invention are not limited to the following examples.

[Chem. 10]

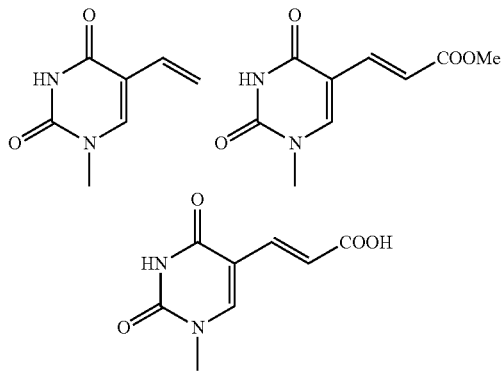

-continued

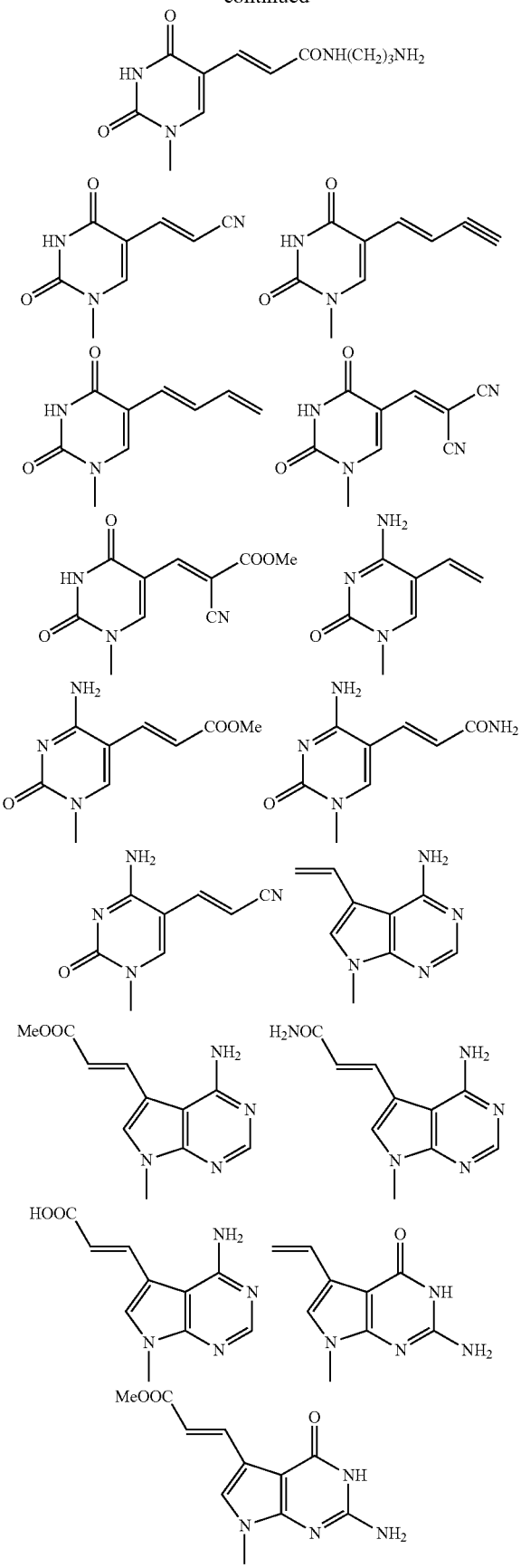

-continued

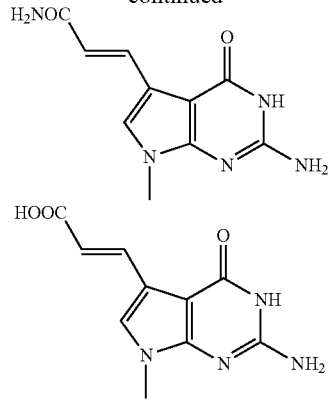

The term "probe" as used herein means a polymer having two or more known nucleoside subunits or nucleic acid base subunits which are linked to each other, and includes DNA and/or RNA or analogues thereof.

The term "analogue" means a non-natural nucleotide having functions similar to those of naturally-occurring nucleotides, such as deoxyribonucleotide (DNA) and ribonucleotide (RNA). That is, nucleotide analogues can form a chain by phosphodiester bonds, as similar to nucleotides, and primers or a probe made of nucleotide analogues can be used for PCR or hybridization, as similar to primers or a probe made of nucleotides alone.

Examples of such nucleotide analogues include PNA (polyamide nucleotide derivative), LNA (BNA), and ENA (2'-O,4'-C-ethylene-bridgednucleic acids), as well as mixtures thereof. PNA is a compound in which the main chain consisting of phosphate and pentose in DNA or RNA is substituted with a polyamide chain. LNA (BNA) is a compound having two cyclic structures in which the oxygen atom at the 2'-position of the ribonucleoside is linked to the carbon atom at the 4'-position thereof via methylene.

The nucleotide analogue is not limited to the above-mentioned analogues, so long as the probe is complementary to the target site and capable of being stably hybridized under hybridization assay conditions. The term "complementary sequence" as used herein means a sequence having a nucleotide sequence capable of forming stable hydrogen bonds under hybridization conditions, and the perfect match between nucleotides of each probe is not needed.

The probe containing a photo-responsive nucleotide in the present invention (i.e., a photocoupling probe) means a probe containing at least one photo-responsive nucleotide, and the probe containing a photo-responsive nucleotide has a sequence complementary to a target site.

The first probe in the present invention (hereinafter sometimes referred to as the photocoupling probe) means a nucleotide probe having a sequence complementary to a target site and containing a photo-responsive nucleotide. The photocoupling probe is not limited, so long as it contains one or more of the photo-responsive nucleotides of the formulae I to VII.

The photocoupling method of the present invention is a photocoupling method, characterized by comprising hybridizing a target site present in a nucleic acid sample, with a first probe having a sequence complementary to the target site and containing a photo-responsive nucleotide, in a reaction solution, and carrying out photocoupling by photo-irradiation, wherein self-assembly (i.e., photocoupling in the self-sequence) caused by the photo-responsive nucleotide contained in the first probe is suppressed.

As the first embodiment of the photocoupling method of the present invention, a crosslinking-type photocoupling method, comprising hybridizing a target site present in a nucleic acid sample, with a first probe having a sequence complementary to the target site and containing a photo-responsive nucleotide, in a reaction solution, and carrying out photocoupling by photo-irradiation, whereby the photocoupling is carried out between a target nucleotide contained in the target site and the photo-responsive nucleotide contained in the first probe, wherein the photocoupling in the self of the first probe is suppressed by co-existing with a second probe being highly complementary to the first probe, may be exemplified.

According to the first embodiment, the photocoupling efficiency between the target nucleotide contained in the target site and the first probe can be improved. For example, the second probe is hybridized to an unreacted first probe that does not hybridize to the target site, under predetermined photocoupling conditions, and as a result, it prevents the first probe from self-assembling to form a secondary structure, and the photocoupling in the self of the first probe by photo-irradiation is suppressed. As a result, the unreacted first probe, in which the photocoupling with the target nucleotide containing the target site does not occur, maintains its photocoupling activity, and thus, the photocoupling efficiency can be improved by continuing the photo-irradiation for a long time, or by repeating the photo-irradiation multiple times during temperature-controlled cycles including denaturation and annealing.

The term "being highly complementary" means a state in which the first probe containing a photo-responsive nucleotide and the second probe are complementary to each other, and a base to be photocoupled with the photo-responsive nucleotide in the self-sequence of the first probe under predetermined photocoupling conditions is hybridized with the complementary second probe. The second probe may be completely complementary to the first probe, or may be preferably complementary to the first probe, but the complete complementary relationship is not needed, if the second probe can be hybridized with the first probe under predetermined photocoupling conditions. For example, in the case where the site(s) that is(are) involved in photocoupling in the self-sequence can be specified, from information such as the type, length, and the like of the first probe sequence, among the nucleotide bases that constitute the first probe, bases other than the base at the site are not necessarily needed to be complementary.

Since the photo-responsive nucleotide in the first probe is photocoupled with the target nucleotide at the target site, it is naturally necessary to design the probes so that the photo-responsive nucleotide is not photocoupled with the second probe. Therefore, it is preferable to design the second probe so as to not inhibit the photocoupling of the photo-responsive nucleotide with the target nucleotide. For example, it may be designed so as to suppress the self-assembly of the first probe containing the photo-responsive nucleotide by the hybridization of the second probe, and so as to lose the binding ability of the photo-responsive nucleotide.

A base capable of photocoupling with the photo-responsive nucleotide is known, or can be identified by those skilled in the art without trial and error. For example, it is known that the photo-responsive nucleotides of formula I or formula II are photocoupled with pyrimidine bases, such as cytosine, thymine, and uracil, the second probe can be designed and used so that it has a complementary sequence to pyrimidine bases in the first probe. The second probe is not necessary to be complementary to all the bases with which the photo-responsive nucleotide in the first probe can be photocoupled in its self-sequence, and it is sufficient to be complementary to at least a base with which the photo-responsive nucleotide in the first probe can be photocoupled in its self-sequence under predetermined photocoupling conditions.

In connection with this, since it is known that consecutive bases are needed in order that the second probe is hybridized with the first probe, it is obvious that the second probe needs complementarity to bases other than a base with which the photo-responsive nucleotide in the first probe can be photocoupled in its self-sequence.

The second probe may suppress the photocoupling in the self-sequence of the first probe, as a single contiguous sequence, or the second probe may be used as a plurality of discontinuous sequences having complementarity to nucleotides capable of photocoupling with the photo-responsive nucleotide contained in the first probe. Such a single contiguous sequence or such a plurality of discontinuous sequences may be appropriately designed and used, in accordance with a known method, depending on an analysis method or photocoupling conditions, in view of a hybridizable nucleotide sequence, its chain length, or the like.

The photo-responsive nucleotide may be placed around the middle of the first probe containing the photo-responsive nucleotide, or at the terminal side of the first probe. In the case where the length of the available first probe is limited in an analysis system utilized (for example, the minimum hybridizable chain length), the second probe capable of being stably hybridized with the first probe can be designed by placing the photo-responsive nucleotide at the terminal side of the first probe.

In the case where, when the photo-responsive nucleotide is placed at the terminus, there is a possibility that the terminal base cannot sufficiently approach the nucleotide to be photocoupled by hybridization, due to the steric hindrance of the photo-responsive nucleotide and, as a result, the photo-responsive nucleotide cannot be photocoupled with the target site, it is preferable that the photo-responsive nucleotide is introduced into the inside of the terminus, more preferably, into the position of the second to fifth base from the terminus.

In conventional technical common knowledge, it has been considered important for probe design that a probe should not have any complementary sequences other than the target site; a probe should not have any complementary sequences in the probe, in order to prevent the probe from forming a secondary structure in its self-sequence; and when two or more probes are used, the number of complementary sequences among them should be reduced.

However, in the photocoupling method of the present invention, with respect to the first probe having a complementary sequence to the target site and containing the photo-responsive nucleotide, it is a surprising effect that the photocoupling efficiency can be improved by using the second probe that has a competitive relationship with the target site, and high complementarity to the first probe.

Whether or not the first probe containing the photo-responsive nucleotide can be photocoupled in its self-sequence can be determined by those skilled in the art, using a known and appropriate method. For example, the second structure of the photocoupling probe can be predicted, and nucleotides that are involved in photocoupling in the self-sequence can be chosen, using a software, such as a calculation of adjacent bases, or a free energy calculation of a given structure. Further, as described below in the Examples, it can be examined whether or not photocoupling in the self-sequence occurs.

The second probe can contain the photo-responsive nucleotide, and it can be designed and used, so that it has a function to suppress self-assembly as the second probe, and another function to be photocoupled as the first probe (photocoupling probe) containing the photo-responsive nucleotide.

The probe containing the photo-responsive nucleotide is sometimes referred to as the first probe in the case where it has an action to be photocoupled, or as the second probe in the case where it has an action to suppress self-assembly. For example, in the case where both a sense strand probe for a target site and an antisense strand probe for the target site contain the photo-responsive nucleotide, when the sense strand probe is regarded as the first probe, the antisense strand probe functions as the second probe, and when the antisense strand probe is regarded as the first probe, the sense strand probe functions as the second probe. In this case, the second probe can be crosslinking-type photocoupled with the target nucleotide in the antisense strand of the target site.

It is not limited to the above method, so long as it is a method for suppressing self-assembly. The photocoupling method of the present invention can be used with appropriate modifications in various analysis methods.

For example, in the case where the sequence of interest is a single strand, such as mRNA, it is sufficient that the photo-responsive nucleotide is contained in at least the first probe, but in the case where the target site is a double strand, such as dsDNA, it is preferable that the photo-responsive nucleotide is contained not only in the first probe, but also in the second probe. For example, in the case of gene analysis where a mutated sequence is detected with high sensitivity by being photocoupled with a wild-type sequence, and it is accompanied by a nucleic acid amplification reaction, the mutated sequence can be detected and identified with higher sensitivity by being photocoupled with both the sense strand and the antisense strand of the wild-type sequence.

In the case where both the first probe and the second probe contain the photo-responsive nucleotides (i.e., they function as the photocoupling probes), the third probe having complementary sequences to the first probe and/or the second probe may be used, so that the photo-responsive nucleotides contained in the first probe and/or the second probe cannot be photocoupled in the self-sequence in non-complementary regions. The third probe may be designed and used in a fashion similar to the embodiment of the second probe.

As the second embodiment of the photocoupling method of the present invention, a ligation-type photocoupling method, comprising hybridizing a target site present in a nucleic acid sample, a first probe having a sequence complementary to the target site and containing a photo-responsive nucleotide, and a fourth probe having a sequence complementary to the target site and containing a target nucleotide, so that they are placed adjacent in a reaction solution, and carrying out photocoupling by photo-irradiation between the target nucleotide contained in the fourth probe and the photo-responsive nucleotide contained in the first probe, wherein photocoupling of the first probe itself is suppressed by co-existing with a second probe being highly complementary to the first probe, may be exemplified.

The second probe having a complementary sequence to the first probe may be used to suppress the assembly in the self-sequence by binding with a base present at the terminus opposite to the terminus into which the photo-responsive nucleotide is incorporated.

As the ligation-type photocoupling method, the method described in WO2007/058326 may be incorporated hereinto and used. The first embodiment of the photocoupling method of the present invention may be appropriately modified, for those skilled in the art, to easily carry out the second embodiment, except that the photocoupling method is a ligation-type method. In such a ligation-type method using the photo-responsive nucleotide, the first probe has the photo-responsive nucleotide at its 3' or 5' terminus, and, in addition to the case where the first probe and the fourth probe are hybridized with the target site, a use method for avoiding the photocoupling by assembly when the photo-responsive nucleotide in the first probe spatially approaches a pyrimidine base, is possible.

Hereinafter, the ligation-type photocoupling method will be explained.

The first probe containing the photo-responsive nucleotide and the fourth probe containing the target nucleotide are placed so as to being hybridized, adjacent to each other, with the predetermined target site, and the photo-responsive nucleotide and the target nucleotide are placed adjacent to each other so that photocoupling by photo-irradiation occurs.

In this case, it is preferable to design the first probe in such a way that the photo-responsive nucleotide is placed at the terminus of the first probe. Further, it is preferable to design the fourth probe so that the target nucleotide capable of photocoupling is placed at its terminus adjacent to the first probe.

It is preferable that the first probe and the fourth probe are adjacent to each other, even without a gap of one base, and a single contiguous nucleotide sequence can be formed by photocoupling when both probes are photo-irradiated.

A further stable nucleotide sequence complementary to that of the target site is formed by linking the first probe containing the photo-responsive nucleotide with the fourth probe containing the target nucleotide by photo-irradiation.

For example, when the first probe containing 5-carboxyvinyl-2'-deoxyuridine (referred to as CVU) as a photo-responsive nucleotide is used, the CVU exhibits photocoupling properties to a pyrimidine base as the target nucleotide, and forms a carbon-carbon double bond with the base moiety of thymine.

The nucleotide sequence to be detected as the target site, the first probe containing CVU, and the fourth probe containing the target nucleotide, are mixed and hybridized with one another. In accordance with the complementarity of nucleotide sequences, the first probe and the fourth probe were placed adjacent to each other against the target site, so that both probes can be photocoupled with each other. When photo-irradiation is carried out in this state, both probes are photocoupled with each other by photo-reaction, and form a single sequence linked by a covalent bond between CVU and a pyrimidine base as the target nucleotide.

In such a ligation-type photocoupling method, photo-responsive nucleotides capable of photocoupling at each terminus of the first probe and the fourth probe may be used, as described above, and the compounds of formulae III to VII may be used as the photo-responsive nucleotides.

The first embodiment or the second embodiment may be carried out alone, but may be carried out in combination thereof. Examples of such a combination include a method in which the first probe containing the photo-responsive nucleotide is subjected to the crosslinking-type photocoupling, and the second probe containing the photo-responsive nucleotide is subjected to the ligation-type photocoupling; and a method in which the first probe containing the photo-responsive nucleotide is subjected to the ligation-type photocoupling, and the second probe containing the photo-responsive nucleotide is subjected to the crosslinking-type photocoupling.

As the third embodiment of the photocoupling method of the present invention, so long as the photocoupling probe can be hybridized with the target site, the photocoupling probe in which the photo-responsive nucleotide that causes self-assembly in the photocoupling probe under predetermined photocoupling conditions is replaced with a nucleotide capable of not being photocoupled with the photo-responsive nucleotide can be designed to suppress photocoupling in the self-sequence. In order to avoid the photocoupling between the sense strand probe and the antisense strand probe, probes in which it is replaced with a nucleotide not capable of being photocoupled with the photo-responsive nucleotide can be designed to suppress the photocoupling between the probes. For example, in the case where the photo-responsive nucleotide is CNVK, it can be carried out by replacing a pyrimidine base with a purine base, such as adenine, guanine, or inosine. The number of bases to be substituted may be appropriately determined in accordance with the number of pyrimidine bases present in the target site or the probe.

In the case where the photo-responsive nucleotide is CNVK, a synthetic base in which the pyrimidine ring of cytosine or thymine, as a base capable of being photocoupled, is artificially converted may be used. In this case, it can be suppressed that the photocoupling probe is photocoupled in its self-sequence, by not causing a [2+2] cycloaddition reaction by photo-irradiation. In this case, examples of the synthetic base which may be used include 5-azo-thymine, 6-azo-thymine, 5-azo-cytosine, and 6-azo-cytosine, which are synthetic bases in which carbon at the 5-position or at the 6-position of the pyrimidine ring is replaced with nitrogen.

The third embodiment may be carried out alone, and may be carried out in a combination thereof with the first embodiment and/or the second embodiment. For those skilled in the art, from known information, taking into consideration which base is the target of the photo-responsive nucleotide used, by what kind of chemical reaction mechanism the photocoupling is carried out, or the like, the base to be targeted may be substituted or modified, and a synthetic base may be appropriately used.

The photocoupling method of the present invention may be carried out in a reaction solution containing a salt with buffering action. Examples of the salt with buffering action include cacodylate, phosphate, and a tris salt. The concentration of the salt with buffering action is preferably 5 to 250 mmol/L. It is preferable that a salt of alkali metal and/or alkaline earth metal is contained. Examples of alkali metal and/or alkaline earth metal include sodium chloride and magnesium chloride. The specific photocoupling reaction between the probe containing the photo-responsive nucleotide and the target site may be promoted by adding an organic solvent, such as DMSO or formamide, to the reaction solution. In connection with this, it is preferable to avoid contamination of a substance suspected of inhibiting a gene analysis method, which is carried out subsequently or simultaneously. In particular, in the case where it is carried out at the same time of a nucleic acid amplification reaction, a reaction composition suitable to the nucleic acid amplification reaction is preferred.

In the photo-irradiation in the photocoupling method of the present invention, light at a wavelength of 350-380 nm in general, preferably light containing a wavelength of 365 nm, and more preferably laser light at a single wavelength of 365 nm, is preferred. In a preferred embodiment, the photo-reaction by photo-irradiation is preferably within 1 second to a few seconds. In connection with this, the photo-reaction time may be extended in view of light transparency of a container and a solution.

The photo-irradiation may be carried out once or more, and the photocoupling efficiency can be raised by repeating it multiple times. The photo-irradiation may be appropriately chosen and carried out by those skilled in the art in accordance with a gene analysis method utilized. For example, an amplification of a wild-type nucleic acid can be suppressed more reliably by repeating photo-irradiation for each amplification cycle in a PCR method. Light may be irradiated in all amplification cycles, or irradiation may be started or terminated from any amplification cycle.

It is important to select the wavelength and the output in photo-irradiation so that the photocoupling probe which has once before been photocoupled with the target nucleotide is not cleaved by a light equilibrium reaction by photo-irradiation. The selection of the wavelength and the output in photo-irradiation may be carried out for those skilled in the art, without undue experimentation.

According to another preferred embodiment, the assembly of the probe with the target site can be carried out efficiently and rapidly by locally increasing the probe concentration, and as a result, the photocoupling efficiency can be raised.

For example, since nucleic acid is negatively charged in a reaction solution, its substantial density can be locally increased, and the photocoupling efficiency can be improved, by coexisting an anionic substance. A negative charged substance, such as an anionic substance, can be used in order to promote hybridization or improve the photocoupling efficiency, in comparison with a non-charged nonionic polymer, such as polyethylene glycol or dextran.

As the promoter for hybridization, a known anionic substance, such as polyacrylic acid, polymethacrylic acid, or a salt thereof, may be used. The anionic substance may exist in a reaction solution where the photocoupling is carried out. Its appropriate concentration range may be examined and determined by those skilled in the art so that it does not affect reactions other than the photocoupling in a gene analysis method for analyzing a gene of interest in a nucleic acid sample. For example, the polyacrylate concentration is preferably about 0.2 to 10% (represented by weight percentage per volume (w/v); the same shall apply hereinafter), and more preferably about 0.5 to 5%. The polymethacrylate concentration is preferably about 1.0 to 50%, and more preferably about 5 to 25%.

The molecular weight of these polymers spans a wide range, and is preferably about 5,000 to 100,000 dalton, and more preferably about 5,000 to 10,000 dalton. With the intension of promoting hybridization in the present invention, various acrylate polymers equivalent thereto, for example, various homopolymers or copolymers of acrylates that are expected to have hybridization-promoting properties, may be used.

It is obvious for those skilled in the art that the method of improving the hybridization efficiency is useful in not only the hybridization of the probe containing the photo-responsive nucleotide with the target site under photocoupling conditions, but also any hybridization.

In the photocoupling of the present invention, the photocoupling efficiency can be improved by streamlining and accelerating the assembly of the photocoupling probe with the target site.

For example, regardless of the content of a nucleotide sequence containing the target site in a nucleic acid sample, the photocoupling efficiency can be improved by increasing the concentration of the photocoupling probe containing the photo-responsive nucleotide. In this case, the probe concentration in photocoupling is preferably about 0.1 µmol/L or more, more preferably about 1 µmol/L or more, and most preferably about 10 µmol/L or more.

As described above, the photocoupling efficiency can be improved by suppressing the photocoupling in the self-sequence of the photocoupling probe containing the photo-responsive nucleotide, or by locally increasing the photocoupling probe concentration, thereby being effectively hybridized with the target site.

The photocoupling method of the present invention can be used in a known gene-analysis method for analyzing a gene of interest in a nucleic acid sample. This includes not only the identification of the presence or absence of the gene of interest, or its sequence, but also the purification or the selective collection of the gene, and is within the scope of design modifications, for those skilled in the art.

Examples of the purification and the selective collection include a pretreatment step for purifying the gene, or selectively collecting nucleic acid containing the target nucleotide in a nucleic acid. The use in these pretreatment steps is very effective in the gene analysis method described below. Therefore, an accurate analysis with high sensitivity can be achieved in a gene analysis method or a gene detection method following the pretreatment, and it is preferred.

As a gene analysis method which may be used in the present invention, a known gene detection method or a known nucleic acid amplification method may be used. As the gene detection method or the nucleic acid amplification method, various methods are known, and for example, an Invader method, a Sniper method, a TaqMan PCR method, a Hybridization Probe method, an SNPIT method, a Pyro-minisequencing method, a Denaturing High Performance Liquid Chromatography (DHPLC) method, an MALDI-TOF/MS method, and a NanoChip method, may be exemplified as a rapidly and high-throughput analyzing method. As another gene analysis method which may be used in the present invention, for example, in the case where an unknown mutated nucleotide is considered present at the target site, the presence or absence of the mutated nucleotide can be judged by determining the nucleotide sequence of an amplified product of the detection region.

As the use of the gene detection method of the present invention, a method of detecting a gene by hybridizing a fluorescent-labeled photocoupling probe complementary to the target site and containing the photo-responsive nucleotide, with the target site; photocoupling the photocoupling probe with the target nucleotide by photo-irradiation; and detecting the fluorescence. For those skilled in the art, the photocoupling method of the present invention can be appropriately modified and used, in accordance with the object of gene analysis, and a known gene detection method can be easily used.

The term "nucleic acid amplification method" as used herein means an amplification reaction of a template nucleic acid utilizing a known polymerase reaction. For example, the photocoupling method of the present invention can be utilized in a known method for suppressing the amplification of nucleic acid, described in WO 2012/033190.

As the use of the photocoupling method of the present invention in a method of amplifying nucleic acid, a use in a method in which when a known nucleic acid amplification method is carried out, using primers capable of amplifying a nucleotide sequence to be detected containing the target site (a nucleotide sequence for amplification), the amplification of a certain nucleotide sequence (for example, wild-type nucleic acid) is suppressed, in accordance with a mutated nucleotide in a gene to be detected, whereas only the other nucleotide sequence(s) (for example, mutated nucleic acid) is selectively amplified, may be exemplified.

Which of a wild-type nucleic acid or a mutated nucleic acid should be selected as the subject to be amplification-suppressed may be appropriately selected in accordance with the object, and therefore, it is not limited. For example, in the case where there is a large deviation in the existence ratio in a nucleic acid sample, the presence or absence of a nucleic acid present in trace amounts can be detected by suppressing a nucleic acid present in large amounts (for example, wild-type nucleic acid), and selectively amplifying only a nucleic acid present in trace amounts (for example, mutated nucleic acid).

For example, by the photocoupling method of the present invention, against a wild-type nucleic acid to be amplification-suppressed (containing the target site), the first probe containing a sequence complementary to the target site and containing the photo-responsive nucleotide is hybridized, and photocoupled with the target nucleotide by photo-irradiation, thereby suppressing the amplification of the wild-type nucleic acid, and only a mutated nucleic acid to be detected is selectively amplified.

Like a TaqMan probe used in a TaqMan method, bases in a sequence may be labeled with a fluorescent substance or a quencher, if necessary. A known probe for detection, such as a TaqMan probe, against a mutated nucleic acid may be used in not only the detection of a nucleic acid of interest, but also the quantification thereof.

The method of amplification-suppressing a specific nucleic acid through the photocoupling method of the present invention may be carried out, simultaneously with the other nucleic acid amplification method, or as a pretreatment step of a nucleic acid amplification method. For those skilled in the art, the photocoupling method of the present invention may be appropriately modified in accordance with the object of gene analysis, and may be easily used in a known gene amplification method.

The primers used in the selective nucleic acid amplification are ones capable of amplifying a nucleotide sequence for amplification of a mutated nucleic acid, and at the same time, ones capable of amplifying a nucleotide sequence for amplification of a wild-type nucleic acid in the wild-type nucleic acid prior to being photocoupled with the probe containing the photo-responsive nucleotide.

Since the molecule having the wild-type sequence is photocoupled with the photocoupling probe containing the photo-responsive nucleotide by photo-irradiation, an elongation reaction does not proceed from the crosslinked base to the 3' terminal side, and therefore, the molecule is not amplified. On the other hand, since most of molecules having mutated sequences are not photocoupled with the photocoupling probe containing the photo-responsive nucleotide by photo-irradiation, an elongation reaction proceeds, and as a result, a selective nucleic acid amplification is achieved.

The amplification primers which may be used in a nucleic acid amplification method are ones capable of amplifying a nucleotide sequence for amplification containing one target site, or two or more target sites, by PCR, and are two kinds of primers between which the nucleotide sequence for amplification is sandwiched. For example, the primers may be two kinds of primers consisting of a forward primer having a nucleotide sequence homologous to the upstream region of the nucleotide sequence for amplification, and a reverse primer having a nucleotide sequence complementary to the downstream region of the nucleotide sequence for amplification. Each concentration of the two primers used in PCR (or a concentration ratio) is not limited, so long as a double-stranded nucleic acid can be obtained as a PCR product, and it is preferable that they are used at the same concentration.

These primers which may be used in PCR may be designed and synthesized by a conventional method, in accordance with the sequence information of a nucleotide sequence containing the nucleotide sequence for amplification. These primers which may be used in PCR are ones in which one or more selected from the group consisting of nucleotides and nucleotide analogues are linked by phosphodiester bonds. The length of the primers is appropriately determined in view of the Tm values of the primers, the kind of the nucleotide sequence for amplification, and the like, and a primer in which 10 to 100 molecules are linked is preferred.

The protocol including the type, amount, and preparation of reagents used in the PCR reaction, reaction conditions, and the like, is carried out in accordance with a conventional method. DNA polymerase used in PCR is not limited, so long as it is one which may be generally used in PCR, and a thermostable polymerase is preferred.

Since the probe containing the photo-responsive nucleotide inhibits a polymerase elongation reaction by photocoupling with the target site caused by photo-irradiation, the probe containing the photo-responsive nucleotide per se does not require resistance to a nuclease activity. Therefore, a polymerase with a nuclease activity can be used. However, in the case where the probe containing the photo-responsive nucleotide functions as a primer, and a polymerase elongation reaction occurs, it is preferable that its Tm value is determined so that the probe is removed from the target molecule at a temperature at which the polymerase elongation reaction occurs, or that the 3' terminus of the probe containing the photo-responsive nucleotide is modified with a substance that inhibits the elongation reaction so that the probe does not function as a primer for amplification. Similarly, in the case where the first probe, the second probe, the third probe, and the fourth probe for the photocoupling method of the present invention are used, it is preferable that the Tm values of these probes are determined and the 3' termini thereof are modified with a substance that inhibits the elongation reaction, so that the probes do not function as a primer for amplification.

The PCR reaction can be carried out in a reaction composition suitable for a normal PCR amplification reaction. Further, a substance that affects the hybridization conditions, such as DMSO or formamide, may be added to a reaction liquid in order to promote the selective amplification reaction.

The photocoupling kit of the present invention is configured so that the photocoupling method of the present invention can be carried out. More particularly, the first embodiment of the photocoupling method of the present invention, the second embodiment, the third embodiment, and the like are carried out. The first probe, the second probe, the third probe, and the fourth probe that constitute the photocoupling kit means the same ones as the first probe, the second probe, the third probe, and the fourth probe in the photocoupling method of the present invention.

The first photocoupling kit of the present invention contains, at least, the first probe (photocoupling probe) having a sequence complementary to the target site in the nucleic sample and containing the photo-responsive nucleotide capable of photocoupling with the target nucleotide in the target site, and the second probe with high complementarity to the first probe.

The second probe containing the photo-responsive nucleotide may be contained. In this case, the second probe also functions as a photocoupling probe.

Further, the third probe that functions as a photocoupling probe and has a sequence complementary to the first probe and/or the second probe may be contained.

The second photocoupling kit of the present invention contains, at least, the first probe (photocoupling probe) having a sequence complementary to the target site in the nucleic sample and containing the photo-responsive nucleotide, the fourth probe containing the target nucleotide capable of being photocoupled with the photo-responsive nucleotide of the first probe, and the second probe with high complementarity to the first probe.

The second probe containing the photo-responsive nucleotide may be contained. In this case, the second probe also functions as a photocoupling probe.

Further, the third probe that functions as a photocoupling probe and has a sequence complementary to the first probe and/or the second probe may be contained.

The third photocoupling kit of the present invention contains, at least, the first probe (photocoupling probe) having a sequence complementary to the target site in the nucleic sample and containing the photo-responsive nucleotide, and the photocoupling probe is a probe in which the photocoupling in its self-sequence is suppressed by replacing a nucleotide that self-assembles with the photo-responsive nucleotide in the photocoupling probe with a nucleotide not capable of photocoupling with the photo-responsive nucleotide.

The photocoupling kit of the present invention may contain a reaction solution, a labeled enzyme, a polymerase for nucleic acid amplification, primers for nucleic acid amplification, and the like, in accordance with a gene analysis method used. For those skilled in the art, appropriate components may be selected to design the kit, in accordance with the composition of a known kit.

EXAMPLES

The present invention now will be further illustrated by, but is by no means limited to, the following Examples, in which CNVK was used as a photo-responsive nucleotide of the photocoupling probe, and the target site was part of an epidermal growth factor receptor (EGFR) gene sequence. Various changes, improvements, and modifications obvious to those skilled in the art are possible without departing from the scope of the appended claims.

In the following Examples, a representation by an amino-acid one-letter code and the position number of the amino acid indicates a wild-type sequence, and in addition to the one-letter code of the original amino acid and the position number of the amino acid, a representation by a combination thereof with the one-letter code of a substituted amino acid indicates a mutated sequence.

Example 1

Confirmation of Photocoupling in Self-Sequence of Photocoupling Probe

Example 1-1

Preparation of Photocoupling Probe

An oligonucleotide consisting of a 100mer sequence the same as part of an exon 21 (ex.21) region of an EGFR gene was synthesized (SEQ ID NO: 1) as a template for photocoupling.

```
[SEQ ID NO: 1] 100 mer oligonucleotide:
                                    (SEQ ID NO: 1)
5'-AGCCAGGAACGTACTGGTGAAAACACCGCAG

CATGTCAAGATCACAGATTTTGGGCTGGCCAAAC

TGCTGGGTGCGGAAGAGAAAGAATACCATGCAGAA-3'
```

Photocoupling probes consisting of a 16mer capable of hybridizing with the synthetic oligonucleotide were prepared as follows. As the photocoupling probes, four types of photo-reactive probes (PREPs) were designed by changing the introduced position of 3-cyanovinylcarbazole-1'-β-deoxyriboside (CNVK) as a photo-responsive nucleotide (SEQ ID NOS: 2 to 5). These PREPs' sequences are shown in Table 1. The position of CNVK introduced into PREP is represented by "n".

CNVK was prepared in accordance with the method described in JP 2009-254279 A, and the synthesis of probes was entrusted to FASMAC Co., Ltd. The structural formula is shown in FIG. 1.

TABLE 1

| PREP | Nucleotide sequence | |
|------|---------------------|---|
| PREP a. | 5'-CAGCAnTTTGGCCAGC-3' | (SEQ ID NO: 2) |
| PREP b. | 5'-CCCAGCAnTTTGGCCA-3' | (SEQ ID NO: 3) |
| PREP c. | 5'-CACCCAGCAnTTTGGC-3' | (SEQ ID NO: 4) |
| PREP d. | 5'-CGCACCCAGCAnTTTG-3' | (SEQ ID NO: 5) |

Example 1-2

Photo-Irradiation to Photocoupling Probe

The PREPs synthesized in Example 1-1. were dissolved in TE at a concentration of 100 μmol/L, and 200 pmol of each solution was separately dispensed into 0.2 mL tubes. Each sample was subjected to photo-irradiation under the following conditions. Photo-irradiation at a photocoupling wavelength of 365 nm was carried out using a UV-LED illuminator (ZUV-C3OH: Omron Corporation), and photo-irradiation at a cleaving wavelength of 312 nm was carried out using a UV transilluminator (Funakoshi Co., Ltd.).
Condition 1: Unirradiation with Light
Each PREP was not subjected to photo-irradiation.
Condition 2: Photocoupling by Photo-Irradiation Each PREP was irradiated with light at 365 nm at room temperature for 1 minute.
Condition 3: Photocoupling by Photo-Irradiation, and Cleavage of Photocoupling by Photo-Irradiation
Each PREP which had been photo-irradiated under condition 2 was irradiated with light at 312 nm at room temperature for 5 minutes.

Example 1-3

Evaluation by Electrophoresis

In order to observe the influence of photo-irradiation, each PREP treated under the conditions described in Example 1-2. was diluted to 10 μmol/L with sterile water, and MultiNA (Shimadzu Corporation) was used to carry out microchip electrophoresis. The gel images are shown in FIG. 2 to FIG. 5.

In all the four types of PREPs, each band of electrophoresis was shifted to the low molecular side by irradiation with light at the photocoupling wavelength. This suggests that the conformation of each PREP apparently changed.

When each PREP was irradiated with light at the photocoupling-cleaving wavelength after the irradiation with light at the photocoupling wavelength, it was confirmed that the band sifted to the low molecular side was returned to the original position prior to the irradiation with light at the photocoupling wavelength (i.e., unirradiation with light). It is considered that the photocoupling that had been formed in each PREP itself was cleaved, and the PREP was returned to the original state.

This phenomenon was confirmed in all the four types of PREPs, and thus, it is considered that it occurs independently of the photocoupling position, i.e., the introduced position of CNVK.

Example 2

Evaluation of Photocoupling Efficiency in Photocoupling Probe Treated with Photo-Irradiation

Example 2-1

Preparation of Photocoupling Probe

PREPa. to PREPd. prepared in Example 1-2. were used as photocoupling probes to be evaluated.

Example 2-2

Photocoupling Reaction of Photocoupling Probe

To 0.2 mL tubes, 2 μL of 100 pmol/L synthetic oligonucleotide, as the target site, was dispensed, 2 μL of 10 μmol/L of PREP, which had been treated under each condition described in Example 1-2, was separately added, and the total volume was adjusted to 20 μL at a final concentration of 1×PCR buffer (10 mmol/L Tris-HCl (pH8.3), 50 mmol/L KCl, 1.5 mmol/L $MgCl_2$, and 0.001% (W/V) gelatin).

The mixtures were heated at 95° C. for 5 minutes, and allowed to stand at 50° C. for 5 seconds, and were irradiated at 50° C. with light at a wavelength of 365 nm, using UV-LED, for 30 seconds. As controls, samples not irradiated with light were provided.

Example 2-3

Preparation of Quantitative PCR Reaction Solution and Reaction Conditions

After 80 μL of sterile water was separately added to 20 μL of each sample solution (including samples for control) prepared in Example 2-2, each mixture was well mixed. From each mixture, 5 μL thereof was used as a template, and a quantitative PCR reaction was carried out, with primers EGFR Ex.21F and Ex.21R using a Light Cycler (Roche).

Light Cycler Fast Start DNA Master SYBER Green I (Roche) was used as a PCR reaction regent. The sequences of the primers were as follows:

```
EGFR ex.21F:
                                        (SEQ ID NO: 6)
5'-GAACGTACTGGTGAAAACACC-3'

EGFR ex.21R:
                                        (SEQ ID NO: 7)
5'-GCATGGTATTCTTTCTCTTCC-3'
```

Example 2-4

Evaluation of Photocoupling Efficiency

The samples that had been subjected to the photocoupling treatment in Example 2-2. and the control samples that had not been subjected to the photocoupling treatment were used as a template to carry out a quantitative PCR reaction under the conditions described in Example 2-3. The target site with which PREP is photocoupled does not function as the template for an amplification reaction, because a polymerase elongation reaction is stopped at the crosslinked position by a covalent bond. Therefore, a fluorescent signal generally rises at a slow cycle in the quantitative PCR reaction, in comparison with the control samples without the photocoupling treatment. The amount of the target site with which PREP is photocoupled can be calculated in accordance with the following equation, and a photocoupling efficiency can be calculated.

$\Delta Ct$=(Ct value of the target site after the photocoupling treatment)−(Ct value of the target site without the photocoupling treatment)

Photocoupling efficiency (%)=$(1-2^{\Delta Ct}) \times 100$

The result of the evaluation of photocoupling efficiency to the target site of each PREP is shown in Table 2.

TABLE 2

| PREP sequence | UV-irradiation conditions | Photocoupling efficiency |
|---|---|---|
| PREP a. | 1 | 91.30% |
|  | 2 | 21.50% |
|  | 3 | 77.30% |
| PREP b. | 1 | 89.30% |
|  | 2 | 0% |
|  | 3 | 83.00% |
| PREP c. | 1 | 86.20% |
|  | 2 | 0.70% |
|  | 3 | 83.30% |
| PREP d. | 1 | 91.30% |
|  | 2 | 34.00% |
|  | 3 | 84.30% |

As a result, it was confirmed in all the PREPs that the photocoupling efficiency was remarkably reduced after the irradiation at the photocoupling wavelength for 1 minute. Further, it was confirmed that the reduced photocoupling efficiency was recovered by the irradiation at the cleaving wavelength for 5 minutes, and the target site was capable of photocoupling.

It is considered from this result that when PREP was irradiated at the photocoupling wavelength, PREP was photocoupled in its self-sequence, and, as a result, the photocoupling ability of the PREP was lost, and the photocoupling efficiency to the target site was remarkably reduced.

Further, it is considered that when the PREP in which photocoupling occurs in its self-sequence was irradiated with light at a photocoupling-cleaving wavelength of 312 nm, the photocoupling formed in the self-sequence was cleaved and returned to the original state, and thus, the reduced photocoupling efficiency was recovered.

Further, the disappearance and recovery of the photocoupling ability was confirmed in all the PREPs, and thus, it was suggested that the photocoupling and cleavage in the self-sequence of PREP can occur independently of the introduced position of CNVK in PREP.

These results are consistent with the facts that the electrophoresis band after the photocoupling reaction was shifted, and the electrophoresis band after the irradiation at the photocoupling-cleaving wavelength was returned to the original position in Example 1.

Example 3

Confirmation of Photocoupling in Self-Sequence of Photocoupling Probe Consisting of Purine Base Alone PREPs consisting of purine bases, which were not capable of photocoupling with CNVK, a photo-responsive nucleotide, were synthesized, and it was confirmed that photocoupling was not formed in the self-sequence of each PREP synthesized, even when it was irradiated with light at the photocoupling wavelength.

Example 3-1

Preparation of Photocoupling Probe

As photocoupling probes, the following three PREPs consisting of purine bases alone, including adenine (A) and guanine (G), were prepared. The sequences of the synthesized PREPs are shown in Table 3. The introduced position (X) of CNVK, a photo-responsive nucleotide, and the chain length (16 mer) were harmonized with one another.

TABLE 3

| PREP | Nucleotide sequence | |
|---|---|---|
| PREP-A | 5'-AAnAAAAAAAAAAAAA-3' | (SEQ ID NO: 8) |
| PREP-G | 5'-GGnGGGGGGGGGGGGG-3' | (SEQ ID NO: 9) |
| PREP-AG | 5'-AGnAGAGAGAGAGAGA-3' | (SEQ ID NO: 10) |

Example 3-2

Photo-Irradiation to Photocoupling Probe

The PREPs synthesized in Example 3-1. were dissolved in TE at a concentration of 100 μmol/L, and 200 pmol of each solution was separately dispensed into 0.2 mL tubes. Each sample was subjected to photo-irradiation under the following conditions. Photocoupling at a photocoupling wavelength of 365 nm was carried out using a UV-LED illuminator.

Condition 1: Unirradiation with Light

Each PREP was not subjected to photo-irradiation.

Condition 2: Photocoupling by Photo-Irradiation

Each PREP was irradiated with light at 365 nm at 4° C. for 3 minutes.

Example 3-3

Evaluation by Electrophoresis

Figure 6:
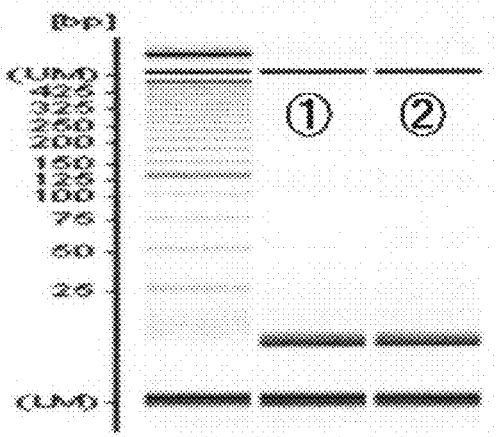
FIG. 6 is a result obtained by carrying out photo-irradiation at a photocoupling-forming wavelength, with respect to a photocoupling probe consisting of only adenine (A), which cannot be a target nucleotide of CNVK, and confirming the resulting sample by electrophoresis.
Figure 7:
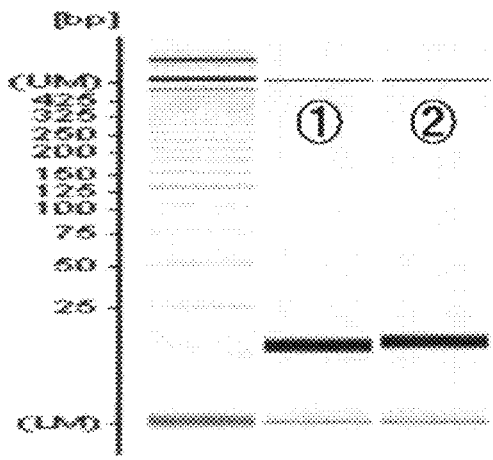
FIG. 7 is a result obtained by carrying out photo-irradiation at a photocoupling-forming wavelength, with respect to a photocoupling probe consisting of only guanine (G), which cannot be a target nucleotide of CNVK, and confirming the resulting sample by electrophoresis.
Figure 8:
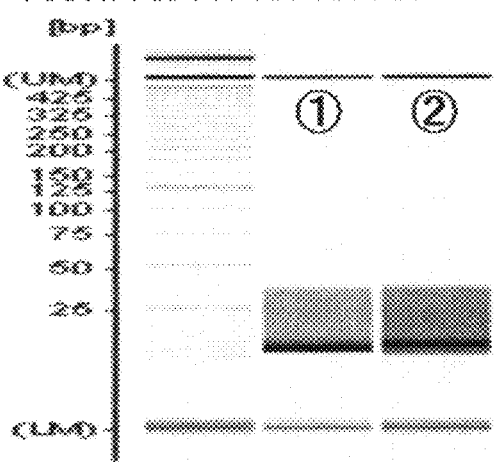
FIG. 8 is a result obtained by carrying out photo-irradiation at a photocoupling-forming wavelength, with respect to a photocoupling probe consisting of only adenine (A) and guanine (G), which cannot be a target nucleotide of CNVK, and confirming the resulting sample by electrophoresis.

In order to observe the influence of photo-irradiation, each PREP treated under the conditions described in Example 3-2. was diluted to 10 μmol/L with sterile water, and MultiNA was used to carry out microchip electrophoresis. The gel images are shown in FIG. 6 to FIG. 8.

In all the three types of PREPs, the electrophoresis bands were not different in mobility, before and after the irradiation with light at the photocoupling wavelength. It was presumed from this result that PREPs consisting of purine bases alone did not contain, in their probe sequences, a base capable of being coupled with CNVK, a photo-responsive nucleotide, and thus, the photocoupling was not formed in their self-sequence.

Example 4

Suppression of Photocoupling in Self-Sequence of Photocoupling Probe Utilizing Complementary Sequence Example 4-1

Preparation of Photocoupling Probe

Figures 9, 10:
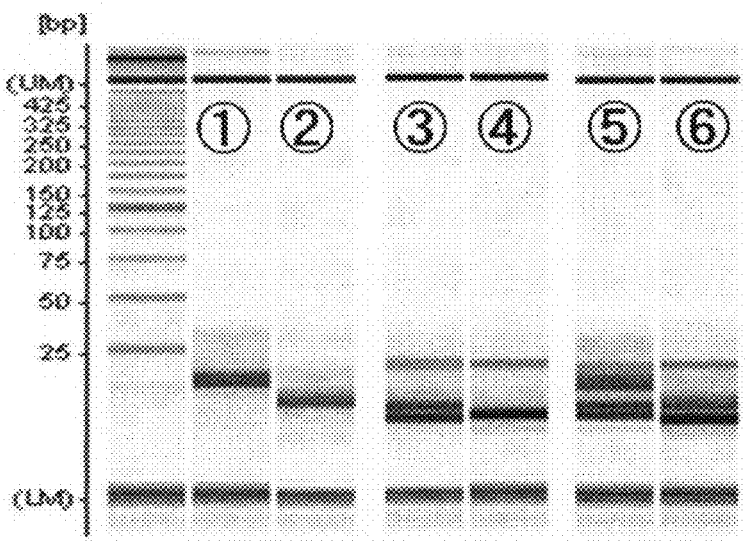
FIG. 9 is photocoupling probes designed so that mutations at three positions of an EGFR gene were target sites. More particularly, it is a drawing showing photocoupling probes designed for each of sense strands and antisense strands, and their complementarity, wherein (1) the nucleic acid sequence encoding the 861st leucine (L861) was the target site, (2) the nucleic acid sequence encoding the 790th threonine (T790) was the target site, and (3) the nucleic acid sequence encoding the 858th leucine (L858) was the target site.
FIG. 10 is a result obtained by carrying out photo-irradiation at a photocoupling-forming wavelength, and confirming the resulting sample by electrophoresis, in the case where the nucleic acid sequence encoding the 861st leucine (L861) of an EGFR gene was the target site, and photocoupling probes were designed for each sense strand and antisense strand.

Nucleotide sequences corresponding to the 790th threonine (T790), the 858th leucine (L858), and the 861st leucine (L861) in the wild-type sequence of an EFGR gene were selected as the target sites. PREPs which were photocoupling probes of the antisense strand (AS strand) capable of hybridizing with the coding strand (i.e., sense strand) of the EGFR gene were designed. Further, PREPs which were photocoupling probes of the sense strand (S strand) capable of hybridizing with the antisense strand of the EGFR gene were designed. The complementarity between the sense-strand-type PREPs and the antisense-strand-type PREPs was changed as the combinations below, and CNVK described in Example 1 was arranged at positions such that corresponding probes were not photocoupled with each other. The sequences of the PREPs actually used as photocoupling probes and the complementarity thereof are schematically shown in FIG. 9. The AS strand in FIG. 9 means that it is complementary to the sense strand of the wild-type EGFR gene sequence, and the S strand means that it is complementary to the antisense strand of the wild-type EGFR gene sequence.

(1) L861: Example of Combination with Low Complementarity (SEQ ID NO: 11)
L861 AS strand:    5'-CTCTTCCGCACCCAnCAG-3'

(SEQ ID NO: 12)
L861 S strand:     5'-TTGGGCTGGCCAAnCTGC-3'

(2) T790: Example of Combination with High Complementarity (SEQ ID NO: 13)
T790 AS strand:    5'-TGAnCTGCGTGATGAG-3'

(SEQ ID NO: 14)
T790 S strand:     5'-CAnCTCATCACGCAGC-3'

(3) L858: Example of Combination with Intermediate Complementarity Between (1) and (2)

(SEQ ID NO: 15)
L858 AS strand:    5'-CAnTTTGGCCAGCCC-3'

(SEQ ID NO: 16)
L858 S strand:     5'-CAnTTTGGGCTGGCCA-3'

Example 4-2

Photo-Irradiation to Photocoupling Probe

Photo-irradiation to photocoupling probes were carried out in accordance with the following conditions.

Condition 1: AS Strand, and Unirradiation with Light

PREPs of the AS strand capable of hybridizing with the sense strand of the EGFR gene, synthesized in Example 4-1, were separately dissolved in TE at a concentration of 10 μmol/L.

Condition 2: AS strand, and photo-irradiation

Each PREP of the AS strand prepared in a fashion similar to Condition 1 was cooled to 4° C. using a Thermal Cycler (manufactured by Applied), and irradiated with light at 365 nm, using a UV-LED illuminator, for 3 minutes.

Condition 3: S Strand, and Unirradiation with Light

PREPs of the S strand capable of hybridizing with the antisense strand of the EGFR gene, synthesized in Example 4-1, were separately dissolved in TE at a concentration of 10 μmol/L.

Condition 4: S Strand, and Photo-Irradiation

Each PREP of the S strand prepared in a fashion similar to Condition 3 was cooled to 4° C. using a Thermal Cycler, and irradiated with light at 365 nm, using a UV-LED illuminator, for 3 minutes.

Condition 5: S Strand and AS Strand, and Unirradiation with Light

PREPs of the AS strand capable of hybridizing with the sense strand of the EGFR gene, and PREPs of the S strand capable of hybridizing with the antisense strand of the EGFR gene, synthesized in Example 4-1, were separately mixed at a concentration of 10 μmol/L each.

Condition 6: S Strand and AS Strand, and Photo-Irradiation

Each PREP solution mixed in a fashion similar to Condition 5 was cooled to 4° C. using a Thermal Cycler, and irradiated with light at 365 nm, using a UV-LED illuminator, for 3 minutes.

Example 4-3

Evaluation by Electrophoresis

Figure 11:
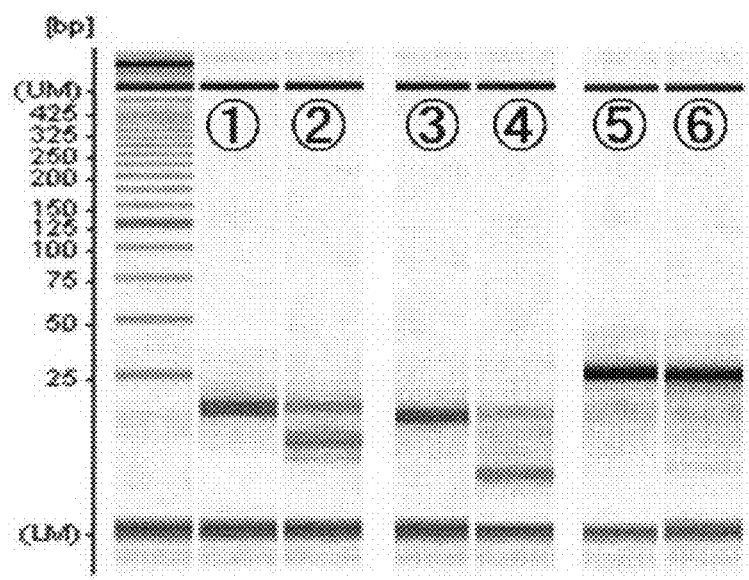
FIG. 11 is a result obtained by carrying out photo-irradiation at a photocoupling-forming wavelength, and confirming the resulting sample by electrophoresis, in the case where the nucleic acid sequence encoding the 790th threonine (T790) of an EGFR gene was the target site, and photocoupling probes were designed for each sense strand and antisense strand.
Figure 12:
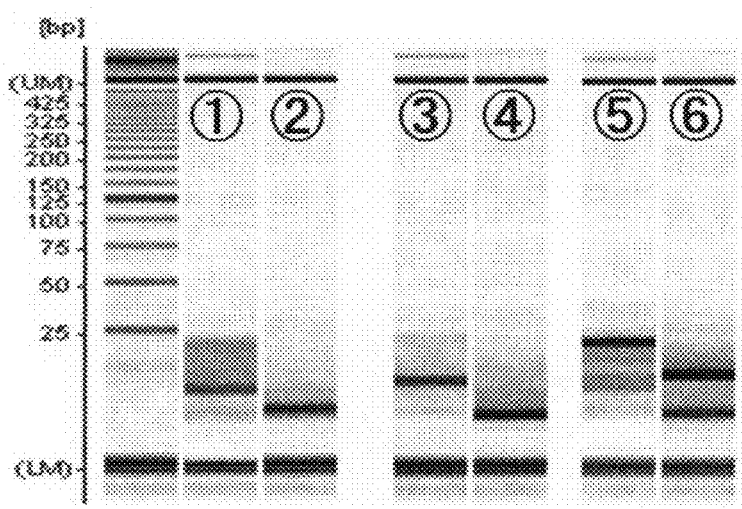
FIG. 12 is a result obtained by carrying out photo-irradiation at a photocoupling-forming wavelength, and confirming the resulting sample by electrophoresis, in the case where the nucleic acid sequence encoding the 858th leucine (L858) of an EGFR gene was the target site, and photocoupling probes were designed for each sense strand and antisense strand.

PREP samples prepared in accordance with the conditions described in Example 4-2. were subjected to microchip electrophoresis, using MultiNA. The gel images are shown in FIG. 10 to FIG. 12. FIG. 10 is the result of (1) the combination of PREPs for L861 as the target site, FIG. 11 is the result of (2) T790, and FIG. 12 is the result of (3) L858.

(1) L861: Combination with Low Complementarity

With respect to the combination with low complementarity, the result of electrophoresis shows a band shift after the photo-irradiation, in both cases of the PREP alone against the sense strand and the PREP alone against the antisense strand, and it was suggested that photocoupling was formed in the self-sequence (lanes 1-4 in FIG. 10).

In condition 5 where the PREP against the sense strand and the PREP against the antisense strand were mixed, the same bands, observed in conditions 1 and 3, were observed at the same positions as those in the case of the PREP alone against the sense strand and the case of the PREP alone against the antisense strand, and it was considered that the PREP against the sense strand was not hybridized with the PREP against the antisense strand.

In condition 6 where the PREP against the sense strand and the PREP against the antisense strand were mixed and photo-irradiated, the same bands were observed at the same positions as those in condition 2 where the PREP against the sense strand was photo-irradiated and in condition 4 where the PREP against the antisense strand was photo-irradiated.

(2) T790: Combination with High Complementarity

With respect to the combination with high complementarity, the result of electrophoresis shows a band shift after the photo-irradiation, in both cases of the PREP alone against the sense strand and the PREP alone against the antisense strand, and it was suggested that photocoupling was formed in the self-sequence (lanes 1-4 in FIG. 11).

In condition 5 where the PREP against the sense strand and the PREP against the antisense strand were mixed, a band was observed at a position different from the positions in the case of the PREP alone against the sense strand in condition 1 where photo-irradiation was not carried out and the case of the PREP alone against the antisense strand in condition 3 where photo-irradiation was not carried out, and it was presumed that the PREP against the sense strand was hybridized with the PREP against the antisense strand.

In condition 6 where the PREP against the sense strand and the PREP against the antisense strand were mixed and photo-irradiated, the same band was observed at the same position as that prior to the photo-irradiation, but no bands were observed at the positions where the bands were detected when photocoupling was formed in the self-sequence by the photo-irradiation to the PREP against the sense strand or the PREP against the antisense strand.

It was suggested from these results that photocoupling would not occur in the self-sequence, when the PREP against the sense strand was hybridized with the PREP against the antisense strand during photo-irradiation.

(3) L858: Combination with Intermediate Complementarity Between (1) and (2)

With respect to the combination with intermediate complementarity, the result of electrophoresis shows a band shift after the photo-irradiation, in both cases of the PREP alone against the sense strand and the PREP alone against the antisense strand, and it was suggested that photocoupling was formed in the self-sequence (lanes 1-4 in FIG. 12).

In condition 5 where the PREP against the sense strand and the PREP against the antisense strand were mixed, a band was observed at a position different from the positions in the case of the PREP alone against the sense strand in condition 1 where photo-irradiation was not carried out and the case of the PREP alone against the antisense strand in condition 3 where photo-irradiation was not carried out, and it was presumed that the PREP against the sense strand was hybridized with the PREP against the antisense strand.

In condition 6 where the PREP against the sense strand and the PREP against the antisense strand were mixed and photo-irradiated, two bands were observed at positions different from the position prior to the photo-irradiation.

The band at the low molecular side (the lower band) was observed at the same position as that in the case where photocoupling was formed in the self-sequence by the photo-irradiation to the PREP against the sense strand or the PREP against the antisense strand, and thus, it was considered that the band was derived from self-assembly of the PREP against the sense strand or the PREP against the antisense strand.

The band at the high molecular side (the upper band) was observed at a position different from those of the bands derived from the self-assembly of the PREP against the sense strand or the PREP against the antisense strand. It was considered from this result that the hybridization between the PREP against the sense strand and the PREP against the antisense strand was maintained, but a band was shifted by photocoupling at the portion where hybridization could not occur.

As described above, in the case where PREPs with low complementarity were mixed and used, it was confirmed that the PREP(s) were photocoupled in the self-sequence(s), even when the PREP alone against the sense strand or the PREP alone against the antisense strand was used, or even when both PREPs were mixed and used.

Even in the case where the PREP against the sense strand and the PREP against the antisense strand had intermediate complementarity, it was suggested that photocoupling was formed in the self-sequence, if a pyrimidine base, such as cytosine or thymine, capable of photocoupling with CNVK existed in unhybridized bases.

It was considered from these results that it would be effective to increase the complementarity between photocoupling probes in order to suppress photocoupling in the self-sequences of the photocoupling probes. Further, it was considered that it would be effective to cover a pyrimidine base(s) capable of photocoupling with CNVK, with its complementary strand, so that the pyrimidine base(s) could not be coupled with CNVK.

Example 5

Confirmation of Photocoupling Using Photocoupling Probe with High Complementarity Example 5-1

Preparation of Photocoupling Probe

The PREPs (target site: T790) with high complementarity, prepared in Example 4-1.(2), were used.

Example 5-2

Preparation of Wild-Type Gene Fragment from EGFR Exon 20 (Ex. 20) Region

Human genomic DNA was prepared from peripheral blood of a healthy person by a conventional method. The resulting DNA was used as a template to amplify an EGFR exon 20 (ex. 20) region comprising a nucleotide sequence corresponding to T790, using a primer set, EGFR ex.20F and EGFR ex.20R, under conventional PCR reaction conditions. The primer sequences used in the PCR reaction are as follows:

```
                                       (SEQ ID NO: 17)
EGFR ex.20F:    5'-CAGAAGCCTACGTGATGG-3'

(SEQ ID NO: 18)
EGFR ex.20R:    5'-ACCTTTGCGATCTGCACAC-3'
```

The resulting PCR amplified product was cloned by inserting it into pGEMT easy Vector (Promega KK) in accordance with the protocol attached thereto.

This plasmid was used as a template to perform amplification using the primer set, EGFR ex.20F and EGFR ex.20R, under conventional PCR reaction conditions, and the amplified product was purified using a PCR Purification Kit (Qiagen) to obtain a linear wild-type gene fragment of EGFR ex. 20 (SEQ ID NO: 19).

The weight concentration of the wild-type gene fragment of EGFR ex. 20 purified using the PCR Purification Kit (Qiagen) was measured using a NanoDrop spectrophotometer (Thermo Scientific), and the copy number of each gene fragment was calculated in view of the amplified fragment length. The thus-obtained fragment was used, as the wild-type nucleic acid, as a reaction template to be examined below.

```
[SEQ ID NO: 19] EGFR ex.20 wild-type fragment
                                       (SEQ ID NO: 19)
5'-
CAGAAGCCTACGTGATGGCCAGCGTGGACAACCCCCACGTGTGCCGCCTG

CTGGGCATCTGCCTCACCTCCACCGTGCAGCTCATCACGCAGCTCATGCC

CTTCGGCTGCCTCCTGGACTATGTCCGGGAACACAAAGACAATATTGGCT

CCCAGTACCTGCTCAACTGGTGTGTGCAGATCGCAAAGGT-3'
```

Example 5-3

Reagent Composition at the Time of Photocoupling Reaction

To 0.2 mL tubes, 2 µL of the target nucleic acid (1×10$^7$ copy/µL) prepared in Example 5-2, and 2 µL each of the PREPs (10 µmol/L) targeting the nucleotide bases corresponding to T790 as shown in Example 4-1.(2) (i.e., T790 AS strand (SEQ ID NO: 3) and T790 S strand (SEQ ID NO: 4)) were added, and the total volume was adjusted to 20 µL at a final concentration of 1×PCR buffer (10 mmol/L Tris-HCl (pH8.3), 50 mmol/L KCl, 1.5 mmol/L MgCl$_2$, and 0.001% (W/V) gelatin).

Example 5-4

Conditions at the Time of Photocoupling Reaction

With respect to the nucleic acid sample solution prepared in Example 5-3, photo-irradiation at a photocoupling wavelength of 365 nm was carried out under two temperature conditions. As control, samples not irradiated with light were provided.
Condition 1: Photo-Irradiation at 50° C.

The samples were heated at 95° C. for 3 minutes, and allowed to stand at 50° C. for 30 seconds, and were irradiated at 50° C. with light for 30 seconds.

Condition 2: Photo-Irradiation at 4° C.

The samples were heated at 95° C. for 3 minutes, and allowed to stand at 4° C. for 1 minute, and were irradiated at 4° C. with light for 30 seconds.

Example 5-5

Confirmation of the Amount of Photocoupling Using Quantitative PCR

To 20 µL of each reaction solution after the photocoupling reaction carried out in Example 5-4., 80 µL of sterile water was added and well mixed. From each mixture, 5 µL thereof was used as a template, and a quantitative PCR reaction was carried out, using a Light Cycler (LC 480 Ver2: Roche).

The reaction solution for quantitative PCR was prepared by mixing the following reagents, and adding sterile water thereto so that the final liquid volume per sample became 25 µL. To 12.5 µL of 2× Premix Ex Taq (registered trademark) (Takara-Bio), 5 pmol each of EGFR ex.20F and EGFR ex.20R, as amplification primers, were added.

Further, 2.5 pmol of a detection probe of which the terminus was fluorescence-labeled was added. The sequence of this detection probe is as follows:

```
Total LNA probe:
                                       (SEQ ID NO: 20)
   5'-Cy5/CTT + CGGC + TGC + CTC/BHQ2-3'
```

The symbol "+" in the sequence means that the base following the symbol is LNA. "Cy5" represents a fluorescent dye as a quencher, and "BHQ2" represents a fluorescence suppressor. The synthesis of the detection probe was entrusted to IDT.

The quantitative PCR reaction was carried out by heating at 95° C. for 10 seconds, and repeating a cycle composed of reactions at 95° C. for 3 seconds and at 58° C. for 30 seconds 45 times.

With respect to each sample, the photocoupling efficiency was evaluated by the ΔCt value, calculated by quantitative PCR in a fashion similar to that of Example 2. The result is shown in FIG. 13.

Figure 13:
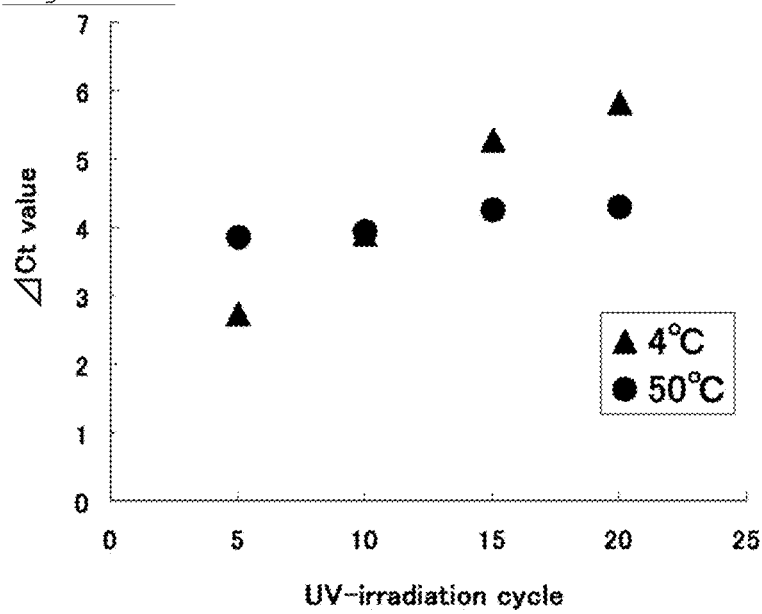
FIG. 13 is a graph showing the photocoupling forming efficiency when the hybridization temperature was changed and the photocoupling was formed, in the case where the nucleic acid sequence encoding the 790th threonine (T790) of an EGFR gene was the target site, and photocoupling probes were designed for each sense strand and antisense strand.

When photo-irradiation at a photocoupling wavelength of 365 nm was carried out at 50° C., it was confirmed that the ΔCt value was substantially constant at about 4, even when a plurality of photo-irradiation was carried out (filled circles in FIG. 13). On the other hand, when the photo-irradiation was carried out at 4° C., it was confirmed that the ΔCt value increased each time the photo-irradiation was carried out (filled triangles in FIG. 13). These results indicate that the amount of photocoupling does not increase at 50° C., even if a plurality of photo-irradiation is carried out, but the amount of photocoupling increases at 4° C. each time the photo-irradiation is carried out.

Therefore, it was considered that, at 4° C., a hybridization formation between PREP complementary strands was maintained, and photocoupling in the self-sequences of the PREPs was suppressed, and thus, the amount of photocoupling increased each time the photo-irradiation was carried out. On the other hand, it was considered that, at 50° C., a hybridization between PREP complementary strands was not sufficiently maintained, and photocoupling in the self-sequences of the PREPs was formed, and thus, the PREPs could not be photocoupled with the template, and then, the amount of photocoupling did not increase even if a plurality of photo-irradiation was carried out.

That is to say, in order to suppress the photocoupling in the self-sequence of a photocoupling probe, it is necessary to increase the complementarity between the photocoupling probe and its complementary strand, and to carry out photo-irradiation under temperature conditions capable of forming a sufficient hybridization between complementary photocoupling probes (or between a photocoupling probe and the second probe complementary to the photocoupling probe).

Example 6

Examination of Additive for Promoting Hybridization

It was suggested from the results of Example 5 that a hybridization between complementary photocoupling probes could not be maintained, when photo-irradiation was carried out at 50° C. Therefore, additives capable of promoting a hybridization between photocoupling probes were examined. Although various additives were examined, the results of a negative-charged polymer (polyacrylic acid: pAAc), which exhibited high effects, are shown below.

Example 6-1

Preparation of Photocoupling Probe

The PREPs (target: nucleotide sequence corresponding to T790) with high complementarity, prepared in Example 4-1.(2), were used.

Example 6-2

Preparation of Wild-Type Gene Fragment from EGFR Exon 20 (Ex. 20) Region

Peripheral blood of a healthy person was used as material, and the wild-type gene fragment from the EGFR ex. 20 region was prepared in a similar fashion to that of Example 5-2.

Example 6-3

Reagent Composition at the Time of Photocoupling Reaction

To 0.2 mL tubes, 2 μL of the wild-type gene fragment of ex. 20 ($1\times10^7$ copy) prepared in Example 6-2, 2 μL each of the PREPs (10 μmol/L) targeting the nucleotide sequence corresponding to T790 as shown in Example 4-1.(2) (i.e., photocoupling probes of T790 AS strand (SEQ ID NO: 13) and T790 S strand (SEQ ID NO: 14)), and 2 μL of 10% (w/w) polyacrylic acid (pAAc) were added, and the total volume was adjusted to 20 μL at a final concentration of 1×PCR buffer (10 mmol/L Tris-HCl (pH8.3), 50 mmol/L KCl, 1.5 mmol/L $MgCl_2$, and 0.001% (W/V) gelatin).

Example 6-4

Conditions at the Time of Photocoupling Reaction

With respect to the nucleic acid sample solution prepared in Example 5-3, photo-irradiation was carried out under the following conditions. As control, samples not irradiated with light at 365 nm were provided.

Condition 1: A nucleic acid sample solution to which polyacrylic acid (pAAc) was added was photo-irradiated at 4° C.
Condition 2: A nucleic acid sample solution without polyacrylic acid (pAAc) was photo-irradiated at 4° C.
Condition 3: A nucleic acid sample solution to which polyacrylic acid (pAAc) was added was photo-irradiated at 50° C.
Condition 4: A nucleic acid sample solution without polyacrylic acid (pAAc) was photo-irradiated at 50° C.

Example 6-5

Confirmation of the Amount of Photocoupling Using Quantitative PCR

The samples in which photocoupling had been carried out by photo-irradiation in Example 5-4. were subjected to quantitative PCR. The quantitative PCR was carried out under the same conditions as those in Example 5.

With respect to each sample, the photocoupling efficiency was evaluated by the ΔCt value, calculated by quantitative PCR in a fashion similar to that of Example 2. The result of the photocoupling at 4° C. is shown in FIG. 14, and the result of the photocoupling at 50° C. is shown in FIG. 15.

Figure 14:
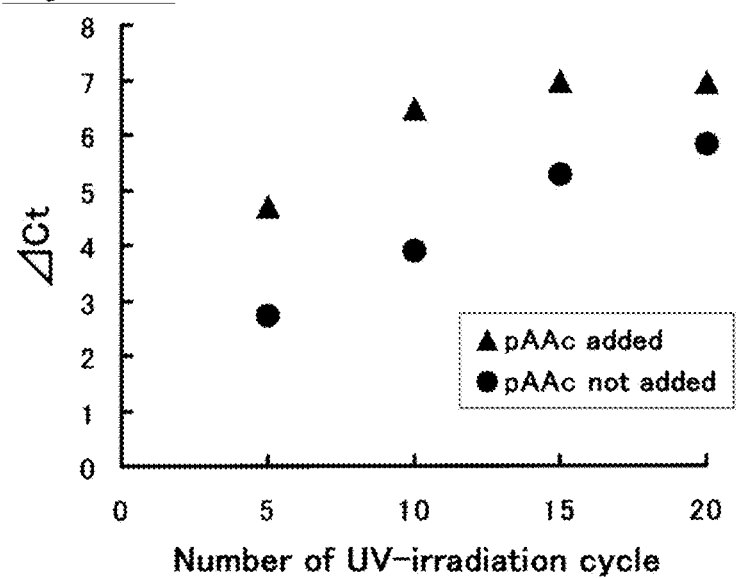
FIG. 14 is a graph showing the photocoupling forming efficiency when polyacrylic acid was added as a promoter for hybridization, a hybridization was carried out at 4° C., and the photocoupling was formed, in the case where the nucleic acid sequence encoding the 790th threonine (T790) of an EGFR gene was the target site, and photocoupling probes were designed for each sense strand and antisense strand.

When photo-irradiation at a photocoupling wavelength of 365 nm was carried out at 4° C., the ΔCt value increased at a cycle of photo-irradiation by the addition of pAAc (filled triangles in FIG. 14). This was because the PREPs could be hybridized with the template more effectively by the addition of pAAc, and the amount of photocoupling per photo-irradiation increased. That is to say, pAAc promotes the hybridization of PREPs with the template.

Figure 15:
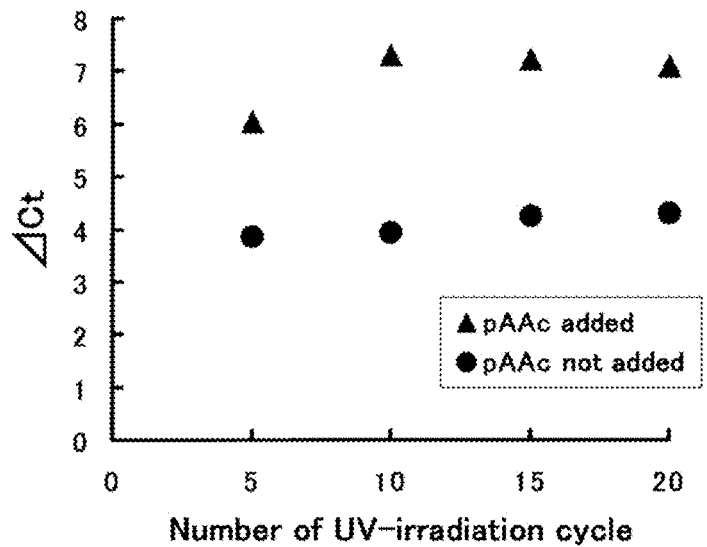
FIG. 15 is a graph showing the photocoupling forming efficiency when polyacrylic acid was added as a promoter for hybridization, a hybridization was carried out at 50° C., and the photocoupling was formed, in the case where the nucleic acid sequence encoding the 790th threonine (T790) of an EGFR gene was the target site, and photocoupling probes were designed for each sense strand and antisense strand.

When photo-irradiation at a photocoupling wavelength of 365 nm was carried out at 50° C., the ΔCt value remarkably increased by the addition of pAAc (filled triangles in FIG. 15). In addition to the fact that the PREPs could be hybridized with the template more effectively by the addition of pAAc, as similar to the result of the photo-irradiation at a photocoupling wavelength of 365 nm at 4° C., it was considered that the promotion of hybridization between the PREP complementary strands enabled the formation of sufficient hybridization between the PREP complementary strands, and as a result, the photocoupling in the self-sequences of the PREPs was suppressed.

It was confirmed from these results that, in order to increase the photocoupling efficiency, it would be effective: to maintain the hybridization between photocoupling probe complementary strands at the time of photo-irradiation at a photocoupling wavelength of 365 nm; to suppress the photocoupling in the self-sequences of photocoupling probes; and to maintain the photocoupling probes in a state capable of photocoupling.

Example 7

Confirmation of Detection Sensitivity of Gene Mutation

As shown in the above-mentioned Examples, it was confirmed that the efficiency in photocoupling to a target site could be improved by suppressing the photocoupling in the self-sequence of a photocoupling probe. Taking this into consideration, in order to examine the effect on the detection sensitivity of gene mutation, T790M of the EGFR gene was used as the target to detect the gene mutation.

Example 7-1

Preparation of Mutated EGFR Gene Fragment

A PrimeSTAR (registered trademark) Mutagenesis Basal Kit (Takara-Bio) was used to introduce a T790M mutation into the wild-type plasmid prepared in Example 5-2, in accordance with a known method. That is to say, the 2639th base of the EGFR gene was changed from cytosine (C) to thymine (T) by the method, and the resulting product was used as a mutated plasmid.

This plasmid was used as the template to carry out an amplification, using the primer set described in Example 4, EGFR ex.20F and EGFR ex.20R, under conventional PCR reaction conditions, to obtain a linear EGFR mutated gene fragment. After the resulting mutated gene fragment was purified using a PCR Purification Kit, the weight concentration thereof was measured using a NanoDrop spectrophotometer, and the copy number of each gene fragment was calculated in view of the amplified fragment length. The thus-obtained fragment was used, as the mutated nucleic acid, as a template to be examined below (SEQ ID NO: 21).

```
EGFR ex.20 mutated fragment
                                    (SEQ ID NO: :21)
5'-
CAGAAGCCTACGTGATGGCCAGCGTGGACAACCCCCACGTGTGCCGCCTG
CTGGGCATCTGCCTCACCTCCACCGTGCAACTCATCATGCAGCTCATGCC
CTTCGGCTGCCTCCTGGACTATGTCCGGGAACACAAAGACAATATTGGCT
CCCAGTACCTGCTCAACTGGTGTGTGCAGATCGCAAAGGT-3'
```

Example 7-2

Preparation of Mutant-Contaminating Sample

The mixing ratio of the wild-type nucleic acid prepared in Example 5-2. to the mutated nucleic acid prepared in Example 7-1. was changed to prepare three types of samples (mutant 1%, mutant 0.1%, and mutant 0.01%), which were used as samples for detecting the mutated nucleic acid. The mixing ratios used of the wild-type nucleic acid to the mutated nucleic acid are shown in Table 4. A sample without the mutated nucleic acid was regarded as a sample of "mutant 0%". The mixing type was represented as the copy number per 1 µL.

TABLE 4

| Wild-type/<br>Mutated | Mutant<br>1% | Mutant<br>0.1% | Mutant<br>0.01% | Mutant<br>0% |
|---|---|---|---|---|
| Mixed amount<br>(copies/1 µL) | $10^7/10^5$ | $10^7/10^4$ | $10^7/10^3$ | $10^7/0$ |
| Mixing ratio | 100:1 | 1000:1 | 10000:1 | 1:0 |

Example 7-3

Preparation of Photocoupling Probe

The photocoupling probes (target: nucleotide sequence corresponding to T790) with high complementarity, prepared in Example 4-1.(2), were used.

Example 7-4

Reagent Composition at the Time of Photocoupling Reaction

To 0.2 mL tubes, 2 µL each of the PREPs targeting the nucleotide sequence corresponding to T790 as shown in Example 4-1.(2) (i.e., T790 AS strand (SEQ ID NO: 13) and T790 S strand (SEQ ID NO: 14)) prepared in Example 7-2, and 2 µL of 10% (w/w) polyacrylic acid (pAAc) were added, and the total volume was adjusted to 20 µL at a final concentration of 1×PCR buffer (10 mmol/L Tris-HCl (pH8.3), 50 mmol/L KCl, 1.5 mmol/L $MgCl_2$, and 0.001% (W/V) gelatin).

Example 7-5

Conditions at the Time of Photocoupling Reaction

With respect to the samples prepared in Example 7-4, photo-irradiation at a photocoupling wavelength of 365 nm was carried out using UV-LED. After heating at 95° C. for 3 minutes, a cycle composed of maintaining at 95° C. for 30 seconds, being allowed to stand at 50° C. for 5 seconds, and photo-irradiating at 50° C. for 30 seconds was repeated 10 times.

Example 7-6

Confirmation of the Amount of Photocoupling Using Quantitative PCR

To 20 µL of each solution prepared in Example 7-5, 80 µL of sterile water was added and well mixed. From each mixture, 5 µL thereof was taken, and 45 µL of sterile water was added thereto. From each mixture, 5 µL thereof was used as a template, and a quantitative PCR reaction was carried out, using a Light Cycler. The quantitative PCR was carried out under the same conditions as those in Examples 5 and 6.

Figure 16:
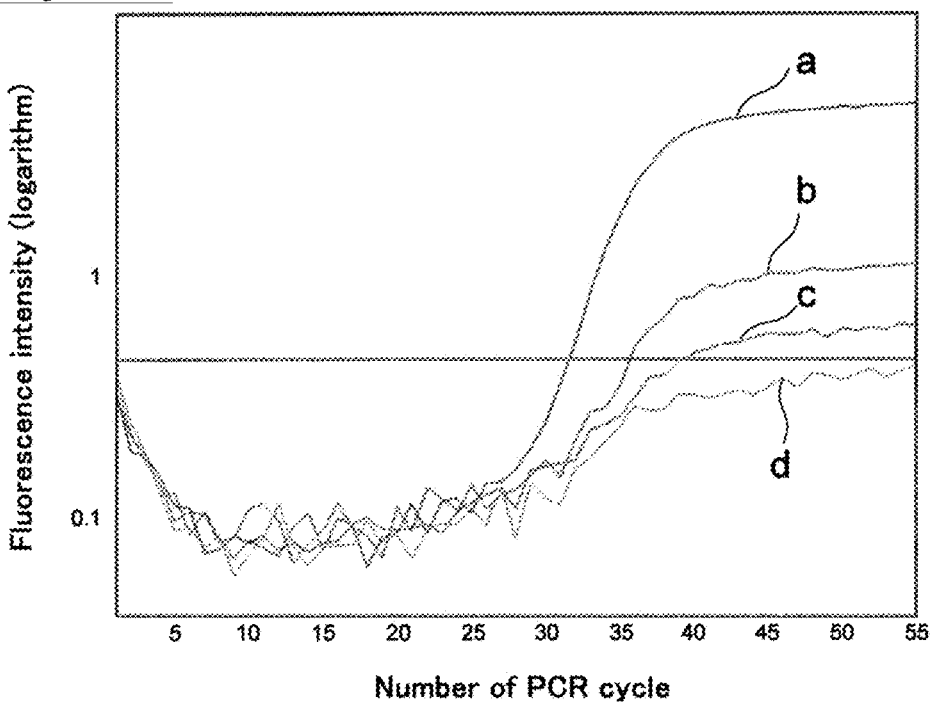
FIG. 16 is a graph showing a result of a quantitative PCR measurement, in the case where the nucleic acid sequence encoding the 790th threonine (T790) of an EGFR gene was the target site, and a gene mutation detection was carried out.

The result is shown in FIG. 16. In FIG. 16, "a" shows the result of mutant 1%, "b" shows the result of mutant 0.1%, "c" shows the result of mutant 0.01%, and "d" shows the result of mutant 0%. The vertical axis of the graph is the logarithm of fluorescence intensity, and the horizontal axis is the number of PCR cycles. In comparison with mutant 0% (wild-type alone), the fluorescent signal increased when the mutant was contaminated. As a result, it was confirmed that the mutant could be detected in a concentration-dependent manner, from mutant 1% to mutant 0.01%. It is considered that it was caused by the fact that the photocoupling efficiency to the wild-type sequence was improved by suppressing the photocoupling in the self-sequences of PREPs.

It became possible to selectively and effectively amplify a mutated nucleic acid by suppressing the photocoupling in the self-sequence of a photocoupling probe, even at an existence ratio of mutant 0.01%, in which it had been very difficult.

As described above, it was confirmed that a mutated gene could be detected with high sensitivity and high accuracy, in accordance with the present method.

Example 8

Evaluation of Inosine-Introduced PREP

Example 8-1

Preparation of Photocoupling Probe (PREP)

The oligonucleotide prepared in Example 1-1, consisting of a 100mer sequence the same as part of an exon 21 (ex.21) region of an EGFR gene, was used as the template to be photocoupled.

The introduced position of inosine was changed to design three types of PREPs (SEQ ID NOS: 23-25) consisting of 16 mer capable of hybridizing with this synthetic oligonucleotide. Another PREP (SEQ ID NO: 22) to which inosine was not introduced was designed as a control for comparison. The sequences of these PREPs are shown in Table 5. The position of a CNVK, a photo-responsive nucleotide, introduced into PREP is represented by "n", and the introduced position of inosine is represented by "I".

TABLE 5

| PREP | Nucleotide sequence | | |
|---|---|---|---|
| PREP e. | 5'-GCAnCCAGCAGTTTGG-3' | (SEQ ID NO: | 22) |
| PREP f. | 5'-GCAnCCAGCAGTTIGG-3' | (SEQ ID NO: | 23) |
| PREP g. | 5'-GCAnCCAGCAGTIIGG-3' | (SEQ ID NO: | 24) |
| PREP h. | 5'-GCAnCCAGCAGIIIGG-3' | (SEQ ID NO: | 25) |

Example 8-2

Photo-Irradiation to PREP

The PREPs synthesized in Example 8-1. were dissolved in TE at a concentration of 100 μmol/L, and 200 pmol of each solution was separately dispensed into 0.2 mL tubes. Each sample was subjected to photo-irradiation under the following conditions. Photo-irradiation at a clamp-forming wavelength of 365 nm was carried out using a UV-LED illuminator (ZUV-C3OH: Omron Corporation).
Condition 1: Unirradiation with Light
Each PREP was not subjected to photo-irradiation.
Condition 2: Photo-Irradiation for Clamp Formation
Each PREP was irradiated with light at 365 nm at 4° C. for 3 minutes.

Example 8-3

Evaluation by Electrophoresis

Figure 17:
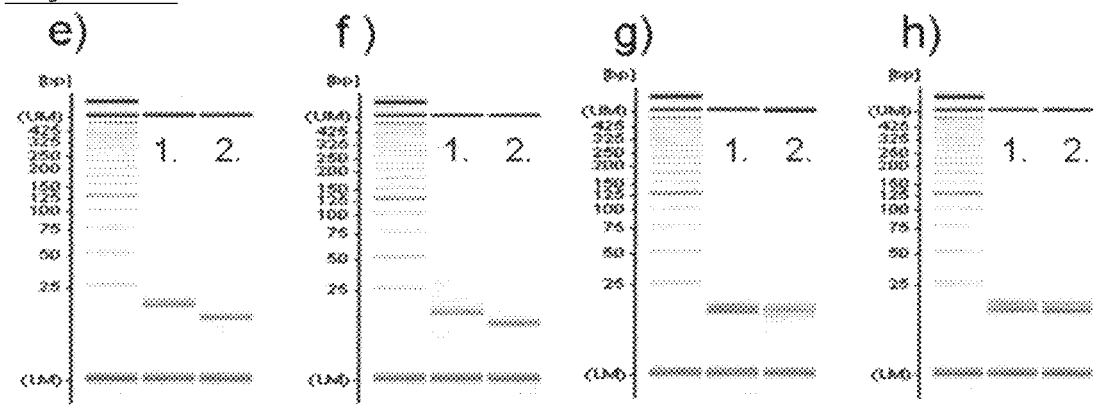
FIG. 17 is a result obtained by carrying out photo-irradiation at a photocoupling-forming wavelength, and confirming the resulting sample by electrophoresis, with respect to a photocoupling probe, which was designed so that part of the exon 21 (ex.21) region of an EGFR gene was the photocoupling forming target, the CNVK as photo-responsive nucleotides was introduced into a position close to the 5' terminus, and pyrimidine bases, capable of photocoupling-forming with CNVK, were replaced with inosine.

In order to observe the influence of photo-irradiation, each PREP treated under the conditions described in Example 8-2. was diluted to 10 μmol/L with sterile water, and MultiNA (Shimadzu Corporation) was used to carry out microchip electrophoresis. The gel images are shown in FIG. 17.

In the PREP to which inosine was not introduced (PREP e.), and the PREP to which inosine was introduced at one position (PREP f.), the band after UV irradiation was shifted to the low molecular side. On the other hand, in the PREPs to which inosine was respectively introduced at two and three positions (PREP g. and PREP h.), no band shift after UV irradiation was not observed. This indicates that an apparent conformational change of PREP occurred by UV irradiation in the PREP to which inosine was not introduced and the PREP to which inosine was introduced at one position, but the conformational change of PREP could be suppressed by the introduction of inosine at two or three positions.

It was indicated from these results that the clamp formation in the self-sequence of PREP could be suppressed by substituting a pyrimidine base, which could function as a crosslinked target in the PREP, with a base which did not function as a crosslinked target, such as inosine.

Example 9

Evaluation of Clamp Formation Efficiency of PREP Treated with Photo-Irradiation

Example 9-1

Preparation of Photocoupling Probe (PREP)

PREP e. and PREP h. prepared in Example 8-1. were used as PREPs to be evaluated.

Example 9-2

Photocoupling Reaction of PREP (Claim Formation Reaction)

To 0.2 mL tubes, 2 μL of 100 pmol/L synthetic oligonucleotide, as a nucleotide sequence having the target site, was dispensed, 2 μL of 100 pmol/L of PREP, which had been treated under each condition described in Example 8-2, was separately added, and the total volume was adjusted to 20 μL at a final concentration of 1×PCR buffer (10 mmol/L Tris-HCl (pH8.3), 50 mmol/L KCl, 1.5 mmol/L MgCl$_2$, and 0.001% (W/V) gelatin).

The mixtures were heated at 95° C. for 5 minutes, and allowed to stand at 45° C. for 5 seconds, and were irradiated at 45° C. with light at a wavelength of 365 nm, using UV-LED, for 30 seconds. As control, samples not irradiated with light were provided.

Example 9-3

Preparation of Quantitative PCR Reaction Solution and Reaction Conditions

After 80 μL of sterile water was separately added to 20 μL of each sample solution (including samples for control) prepared in Example 9-2, each mixture was well mixed. From each mixture, 5 μL thereof was mixed with 45 μL of sterile water. From each mixed sample, 5 μL thereof was used as a template, and a quantitative PCR reaction was carried out, using a Light Cycler (LC 480 Ver2: Roche).

The reaction solution for quantitative PCR was prepared by mixing the following reagents, and adding sterile water thereto so that the final liquid volume per sample became 25 μL. To 12.5 μL of 2× Premix Ex Taq (registered trademark) (Takara-Bio), 5 pmol each of EGFR ex.21F (SEQ ID NO:6) and EGFR ex.21R (SEQ ID NO:7), as amplification primers, were added.

Further, 2.5 pmol of a detection probe of which the terminus was fluorescence-labeled was added. The sequence of this detection probe is as follows:

Total LNA probe:
```
                                    (SEQ ID NO: 26)
5'-Cy5/CAGCATGT + CAAGA + TCACAGA/BHQ_2-3'
```

The symbol "+" in the sequence means that the base following the symbol is LNA. "Cy5" represents a fluorescent dye, and "BHQ2" represents a fluorescence suppressor. The synthesis of the detection probe was entrusted to IDT.

The quantitative PCR reaction was carried out by heating at 95° C. for 10 seconds, and repeating a cycle composed of reactions at 95° C. for 3 seconds and at 56° C. for 30 seconds 45 times.

Figure 18:
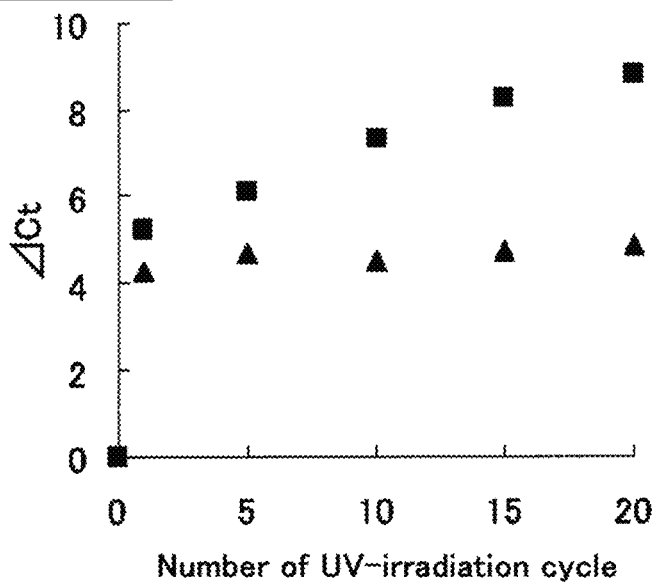
FIG. 18 is a graph showing the photocoupling forming efficiency when photocoupling probes designed for an EGFR gene in Example 8-1. were used to form photocoupling.

With respect to each sample, the clamp forming efficiency was evaluated by the ΔCt value, calculated by quantitative PCR in a fashion similar to that of Example 2. The result is shown in FIG. 18.

The sequences of the primers are as follows:

```
                                    (SEQ ID NO: 6)
EGFR ex.21F:    5'-GAACGTACTGGTGAAAACACC-3'

(SEQ ID NO: 7)
EGFR ex.21R:    5'-GCATGGTATTCTTTCTCTTCC-3'
```

When PREP e. to which inosine was not introduced was used, it was confirmed that the ΔCt value was substantially constant at about 4, even when a plurality of photo-irradiation was carried out (triangles in FIG. 18). On the other hand, when PREP h. to which inosine was introduced was used, it was confirmed that the ΔCt value increased each time the number of UV irradiation increased (squares in FIG. 18)

In connection with this, it is considered that, in the PREP to which inosine was not introduced, a clamp formation in the self-sequence of the PREP occurred, and thus, the amount of clamp formation of the PREP to the template did not increase even when a plurality of photo-irradiation was carried out, whereas in the PREP to which inosine was introduced, the clamp formation in the self-sequence of the PREP was suppressed, and the PREP became a state capable of sufficiently forming a clamp to the template, and thus, the amount of clamp formation increased depending on the number of UV irradiation.

That is to say, it was indicated that the photocoupling in the self-sequence of PREP could be suppressed, and the amount of clamp formation of PREP could be increased, by substituting a crosslinked target base in the self-sequence of PREP, with a base which did not function as a target nucleotide for photocoupling, such as inosine.

Example 10

Confirmation of Clamp Formation Using PREP with High Complementarity

Example 10-1

Preparation of Photocoupling Probe (PREP)

The nucleotide sequence corresponding to the 861st leucine (L861) of an EGFR gene (wild-type) was selected as the target site. The sequence of PREP e. designed in Example 8-1. was regarded as a PREP of the antisense strand (AS strand), which was hybridized with the coding strand (i.e., sense strand) of the EGFR gene. Additionally, a PREP of the sense strand (S strand), which was hybridized with the antisense strand of the EGFR gene, was designed (SEQ ID NO: 27). The position of CNVK introduced is represented by "n".

```
                                    (SEQ ID NO: 22)
L861 AS strand:    5'-GCAnCCAGCAGTTTGG-3'

(SEQ ID NO: 27)
L861 S strand:     5'-CTGnCCAAACTGCTGG-3'
```

Additionally, PREPs in which the complementarity between a PREP of the sense strand and a PREP of the antisense strand was completely complementary, CNVK was placed at a position where the PREPs could not be photocoupled with each other, and the target nucleotide originally capable of being photocoupled with CNVK of each PREP was replaced with inosine, were designed. The position of CNVK introduced is represented by "n", and the position of inosine introduced is represented by "I".

```
                                    (SEQ ID NO: 28)
L861 AS strand:    5'-GCAnCCAGCAGTITGG-3'

(SEQ ID NO: 29)
L861 S strand:     5'-CCAAnCTGCTGGGIGC-3'
```

Figure 19:
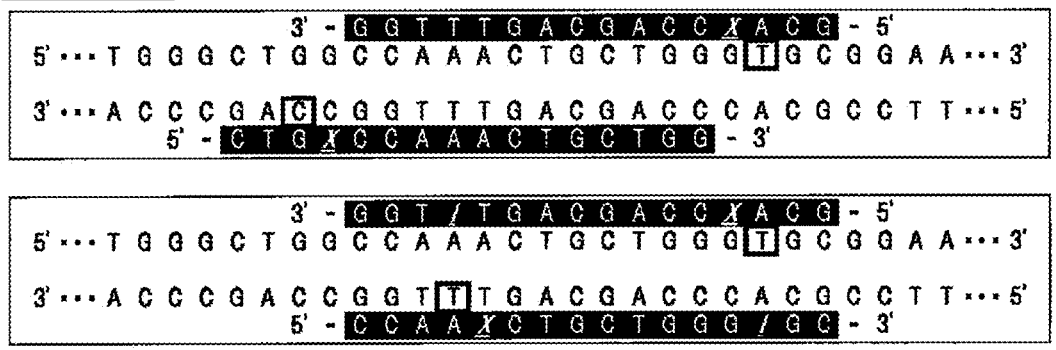
FIG. 19 is a drawing showing photocoupling probes designed for each of sense strands and antisense strands, and their complementarity, wherein the nucleic acid sequence encoding the 861st leucine (L861) in the exon 21 (ex.21) region of an EGFR gene was the target site.

The sequences of the PREPs which were actually used as clamp probes and their complementarity are schematically shown in FIG. 19.

Example 10-2

Preparation of Wild-Type Gene Fragment in EGFR Exon 21 (Ex.21) Region

Human genomic DNA was prepared from peripheral blood of a healthy person by a conventional method. The resulting DNA was used as a template to amplify an EGFR exon 21 (ex. 21) region comprising a nucleotide sequence corresponding to L861, using a primer set, EGFR ex.21F and EGFR ex.21R, under conventional PCR reaction conditions. The primer sequences used in the PCR reaction are as follows:

```
EGFR ex.21F (out):
                                    (SEQ ID NO: 30)
5'-GCATGAACTACTTGGAGGAC-3'

EGFR ex.21R (out):
                                    (SEQ ID NO: 31)
5'-ACCTAAAGCCACCTCCTTAC-3'
```

The resulting PCR amplified product was cloned by inserting it into pGEMT easy Vector (Promega KK) in accordance with the protocol attached thereto.

This plasmid was used as a template to perform amplification using the primer set, EGFR ex.21F and EGFR ex.21R, under conventional PCR reaction conditions, and the amplified product was purified using a PCR Purification Kit (Qiagen) to obtain a linear wild-type gene fragment of EGFR ex. 21 (SEQ ID NO: 32).

The weight concentration of the wild-type gene fragment of EGFR ex. 21 purified using the PCR Purification Kit (Qiagen) was measured using a NanoDrop spectrophotometer (Thermo Scientific), and the copy number of each gene fragment was calculated in view of the amplified fragment length. The thus-obtained fragment was used, as the wild-type nucleic acid, as a reaction template to be examined below.

[SEQ ID NO: 32] EGFR ex.21 wild-type fragment (SEQ ID NO: 32)

5'-
GCATGAACTACTTGGAGGACCGTCGCTTGGTGCACCGCGACCTGGCAGCC

AGGAACGTACTGGTGAAAACACCGCAGCATGTCAAGATCACAGATTTTGG

GCTGGCCAAACTGCTGGGTGCGGAAGAGAAAGAATACCATGCAGAAGGAG

GCAAAGTAAGGAGGTGGCTTTGGT-3'

Example 10-3

Reagent Composition at the Time of Photocoupling Reaction

To 0.2 mL tubes, 2 µL of the target nucleic acid ($1 \times 10^7$ copy/µL) prepared in Example 10-2, and 2 µL each of the PREPs (100 µmol/L) targeting the nucleotide bases corresponding to L861 as shown in Example 10-1. (i.e., L861 AS strand (SEQ ID NO: 28) and L861 S strand (SEQ ID NO: 29)) were added, and the total volume was adjusted to 20 µL at a final concentration of 1×PCR buffer (10 mmol/L Tris-HCl (pH8.3), 50 mmol/L KCl, 1.5 mmol/L $MgCl_2$, and 0.001% (W/V) gelatin).

Example 10-4

Conditions at the Time of Photocoupling Reaction

The nucleic acid sample solutions prepared in Example 10-3. were heated at 95° C. for 5 minutes, and allowed to stand at 45° C. for 5 seconds, and were irradiated at 45° C. with light at a wavelength of 365 nm, using UV-LED, for 30 seconds. As controls, samples not irradiated with light were provided.

Example 10-5

Confirmation of the Amount of Clamp Using Quantitative PCR

To 20 µL of each reaction solution after the photocoupling reaction in Example 10-4., 80 µL of sterile water was added and well mixed. From each mixture, 5 µL thereof was taken, and 45 µL of sterile water was added thereto. From each mixture, 5 µL thereof was used as a template, and a quantitative PCR reaction was carried out, using a Light Cycler (LC 480 Ver2: Roche).

The reaction solution for quantitative PCR was prepared by mixing the following reagents, and adding sterile water thereto so that the final liquid volume per sample became 25 µL. To 12.5 µL of 2× Premix Ex Taq (registered trademark) (Takara-Bio), 5 pmol each of EGFR ex.21F and EGFR ex.21R, as amplification primers, were added. Further, 2.5 pmol of a detection probe of which the terminus was fluorescence-labeled was added. The probe (SEQ ID NO: 26) described in Example 9 was used as the detection probe, and the quantitative PCR reaction was carried out under the same conditions as those in Example 9-2.

Figure 20:
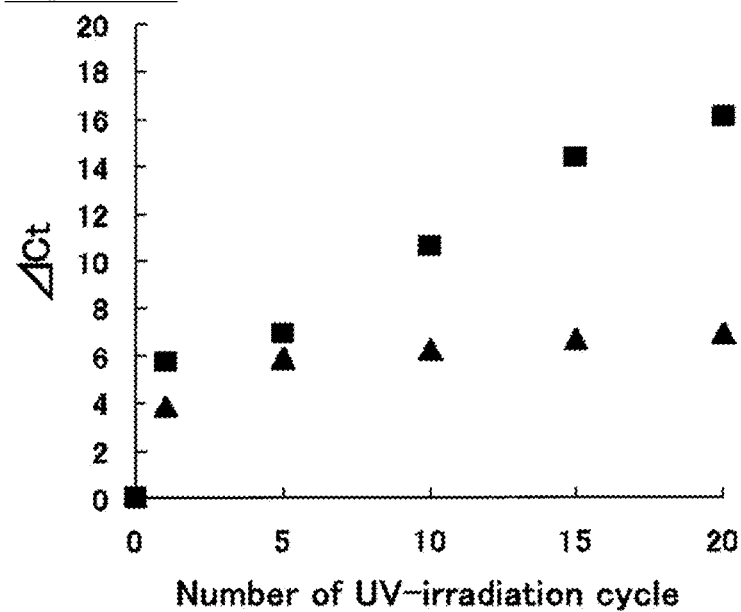
FIG. 20 is a graph showing the photocoupling forming efficiency when photocoupling probes designed for an EGFR gene in Example 10-1. were used to form photocoupling.

With respect to each sample, the clamp forming efficiency was evaluated by the ΔCt value, calculated by quantitative PCR in a fashion similar to that of Example 2. The result is shown in FIG. 20.

With respect to the PREP designed by conventional design techniques (filled triangle), the ΔCt value became saturated at a certain place, even when a plurality of irradiations with UV was carried out. On the other hand, it was confirmed that when the PREP which contained inosine and was completely complementary was used, the ΔCt value could be increased each time the UV-irradiation was carried out.

It is considered that the clamp formation in the self-sequence of each PREP could be suppressed by introducing inosine into the PREPs and increasing the complementarity of the PREPs. It was also confirmed from these results that: to maintain the hybridization between PREP complementary strands at the time of photo-irradiation at 365 nm as the clamp formation wavelength; to suppress the clamp formation in the self-sequence; and to keep the PREPs a state capable of forming clamp; were effective in improving the clamp forming efficiency.

INDUSTRIAL APPLICABILITY

The present invention relates to a method of improving photocoupling efficiency, using a probe containing photo-responsive nucleotides, and gene analysis can be carried out with both high sensitivity and high accuracy. For example, it can be used in selectively detecting a mutated gene present in trace amounts, mixed with a wild-type gene present in large amounts. Additionally, a target gene can be detected from a nucleic acid sample that is difficult to detect by a conventional evaluation method, because the target gene is present in trace amounts.

Since such an analysis above is possible, not only specimens with high invasiveness, such as tissues or biopsy material excised by surgery, but also specimens in which a target nucleic acid is present in trace amounts, such as blood samples, can be handled as samples, and thus, confirmation of a therapeutic effect or monitoring inspection, which was difficult, can be carried out. This allows for the realization of personalized medicine, by applying it to, for example, an early detection of cancer, or drug efficacy evaluation, such as drug susceptibility and drug response, for individual patients.

Although the present invention has been described with reference to specific embodiments, various changes and modifications obvious to those skilled in the art are possible without departing from the scope of the appended claims.

FREE TEXT IN SEQUENCE LISTING

The nucleotide sequences of SEQ ID NOS: 2 to 5 of the sequence listing are artificially synthesized probe sequences, and are respectively PREPa. (the sixth n is CNVK), PREPb. (the eighth n is CNVK), PREPc. (the tenth n is CNVK), and PREPd. (the twelfth n is CNVK). The nucleotide sequences of SEQ ID NOS: 8 to 10 are artificially synthesized probe sequences, and are respectively PREP-A (the third n is CNVK), PREP-G (the third n is CNVK), and PREP-AG (the third n is CNVK). The nucleotide sequences of SEQ ID NOS: 11 to 16 are artificially synthesized probe sequences, and are respectively probe L861 AS (the fifteenth n is CNVK), probe L861 S (the fourteenth n is CNVK), probe T790 AS (the fourth n is CNVK), probe T790 S (the third n is CNVK), probe L858 AS (the third n is CNVK), and probe L858 S (the third n is CNVK). The nucleotide sequence of SEQ ID NO: 20 is an artificially synthesized probe sequence, and is Total LNA probe (the fourth C, the eighth T, and the eleventh C are LNAs). The nucleotide sequences of SEQ ID NOS: 22 to 25 are artificially synthesized probe sequences, and are respectively PREPe. (the fourth n is CNVK), PREPf. (the fourth n is CNVK, and the fourteenth n is inosine), PREPg. (the fourth n is CNVK, and the thirteenth n and the fourteenth n are inosines), and PREPh. (the fourth n is CNVK, and the twelfth to fourteenth n's are inosines). The nucleotide sequence of SEQ ID NO: 26 is an artificially synthesized probe sequence, and is Total LNA probe (the ninth C and the fourteenth T are LNAs). The nucleotide sequences of SEQ ID NOS: 27 to 29 are artificially synthesized probe sequences, and are respectively probe L861 S (the fourth n is CNVK), probe T861 AS (the fourth n is CNVK, and the thirteenth n is inosine), and probe T861 S (the fifth n is CNVK, and the fourteenth n is inosine).

The invention claimed is:

1. A photocoupling method, comprising hybridizing a target site present in a nucleic acid sample with a first probe having a sequence complementary to the target site and containing a photo-responsive nucleotide, in a reaction solution, and carrying out photocoupling by photo-irradiation, wherein self-assembly caused by the photo-responsive nucleotide contained in the first probe is suppressed by co-existing with a second probe being highly complementary to the first probe, and wherein the first probe is designed so that the photo-responsive nucleotide in the first probe is not photocoupled with the second probe, and wherein:

the second probe is hybridized to an unreacted first probe that does not hybridize to the target site, and as a result, it prevents the first probe from self-assembling to form a secondary structure, and the photocoupling in the self of the first probe by photo-irradiation is suppressed, and the unreacted first probe, in which the photocoupling with a target nucleotide containing the target site does not occur, maintains its photocoupling activity.

2. The photocoupling method according to claim 1, wherein being highly complementary means a state in which the first probe and the second probe are complementary to one another, and a base to be photocoupled with the photo-responsive nucleotide itself in the first probe under predetermined photocoupling conditions hybridizes with the second probe.

3. The photocoupling method according to claim 1, wherein a target nucleotide contained in the target site present in the nucleic acid sample is photocoupled with the photo-responsive nucleotide contained in the first probe.

4. The photocoupling method according to claim 1, wherein the second probe contains a photo-responsive nucleotide.

5. The photocoupling method according to claim 1, wherein the first probe and the second probe contain photo-responsive nucleotides, and a third probe having a sequence complementary to the first probe and/or the second probe is used so that the photo-responsive nucleotide or the photo-responsive nucleotides present in the first probe and/or the second probe cannot be photocoupled itself in a non-complementary region between the first probe and the second probe.

6. The photocoupling method according to claim 1, comprising hybridizing a target site present in a nucleic acid sample, a first probe having a sequence complementary to the target site and containing a photo-responsive nucleotide, and a fourth probe having a sequence complementary to the target site and containing a target nucleotide, so that they are placed adjacent in a reaction solution, and carrying out photocoupling by photo-irradiation between the target nucleotide contained in the fourth probe and the photo-responsive nucleotide contained in the first probe, wherein self-assembly caused by the photo-responsive nucleotide contained in the first probe is suppressed by co-existing with a second probe being highly complementary to the first probe, and wherein the first probe is designed so that the photo-responsive nucleotide in the first probe is not photocoupled with the second probe.

7. The photocoupling method according to claim 1, comprising using the first probe, and wherein a nucleotide that self-assembles with the photo-responsive nucleotide in the first probe is substituted with a nucleotide not capable of photocoupling with the photo-responsive nucleotide, and wherein photocoupling of the first probe itself is suppressed.

8. The photocoupling method according to claim 7, wherein the nucleotide is not capable of photocoupling with the photo-responsive nucleotide is a purine base.

9. The photocoupling method according to claim 7, wherein the nucleotide is not capable of photocoupling with the photo-responsive nucleotide is a synthetic base obtained by artificially converting a pyrimidine ring.

10. The photocoupling method according to claim 1, wherein an anionic substance is contained in the reaction solution.

11. The photocoupling method according to claim 1, wherein at least one photocoupling probe is contained at a concentration of 0.1 μmol/L or more in the reaction solution.

12. A method for gene analysis, said method comprising using the photocoupling method according to claim 1.

13. The method for gene analysis according to claim 12, which is a method for gene detection or a method for nucleic acid amplification.

14. A method for mutated nucleic acid detection, wherein the method for nucleic acid amplification described in claim 13 is a method for detecting the presence or absence of the mutated nucleic acid, by selectively amplifying a nucleotide sequence for amplification containing a target site of the mutated nucleic acid.

* * * * *